United States Patent [19]

Weller, III et al.

[11] Patent Number: 4,560,506

[45] Date of Patent: Dec. 24, 1985

[54] MERCAPTOCYCLOALKYLCARBONYL AND MERCAPTOARYLCARBONYL DIPEPTIDES

[75] Inventors: Harold N. Weller, III; Eric M. Gordon, both of Pennington; Norma G. Delaney, Princeton, all of N.J.

[73] Assignee: E. R. Squibb & Sons, Inc., Princeton, N.J.

[21] Appl. No.: 614,090

[22] Filed: May 25, 1984

[51] Int. Cl.⁴ .................. C07C 103/52; C07D 207/00; C07D 277/04; C07D 209/44; C07D 211/06; C07D 213/22; C07D 241/36; C07D 209/02; C07D 277/60; C07D 231/06; C07D; C07D 403/30; C07D 499/00; C07G 7/00

[52] U.S. Cl. .................. 260/112.5 R; 548/533; 548/201; 548/470; 548/452; 548/147; 548/379; 548/315; 546/205; 546/260; 260/239 A; 260/112 R; 544/349

[58] Field of Search .................. 260/112.5 R, 239 A, 260/112 R; 548/533, 201, 470, 452, 147, 379, 315; 546/205, 260; 544/349

[56] References Cited

U.S. PATENT DOCUMENTS

| | | | |
|---|---|---|---|
| 4,248,883 | 2/1981 | Sawayama et al. | 424/274 |
| 4,440,941 | 4/1984 | Suh et al. | 560/20 |
| 4,456,595 | 6/1984 | Weller et al. | 424/177 |
| 4,499,079 | 2/1985 | Gordon et al. | 514/2 |

FOREIGN PATENT DOCUMENTS 2045771 1/1983 United Kingdom .

OTHER PUBLICATIONS

Biochem. Biophys. Res. Commun. 125 82-89, (1984).

*Primary Examiner*—Delbert R. Phillips
*Attorney, Agent, or Firm*—Lawrence S. Levinson; Stephen B. Davis

[57] ABSTRACT

Compounds of the formula

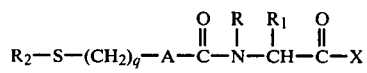

wherein A is a cycloalkyl ring, a substituted cycloalkyl ring, a phenyl ring, or a substituted phenyl ring and

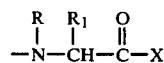

are various dipeptide groups are disclosed. The compounds possess angiotensin converting enzyme inhibition activity and depending upon the terminal amino acid may also possess enkephalinase inhibition activity.

24 Claims, No Drawings

MERCAPTOCYCLOALKYLCARBONYL AND MERCAPTOARYLCARBONYL DIPEPTIDES

BACKGROUND OF THE INVENTION

Ondetti et al. in U.K. Pat. No. 2,045,771 disclose mercaptoacyldipeptides of the formula

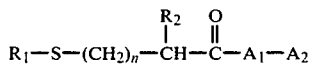

wherein $R_1$ is hydrogen, alkanoyl, benzoyl, or forms a symmetrical disulfide, $R_2$ is hydrogen, alkyl, or phenylalkyl, n is zero or one, and $A_1$ and $A_2$ each is an α-imino or α-amino acid residue joined through a peptide bond. The compounds possess angiotensin converting enzyme inhibition activity.

Sawayama et al. in U.S. Pat. No. 4,248,883 disclose 1-(3-mercapto-2-methylpropanoyl)prolyl amino acid derivatives of the formula

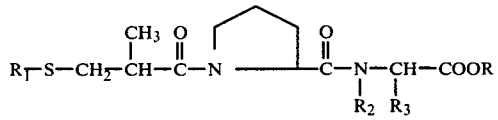

wherein $R_2$ is hydrogen or lower alkyl, $R_3$ is hydrogen, phenyl, lower alkyl, or substituted lower alkyl, or $R_2$ and $R_3$ join together to complete a heterocyclic ring. These compounds are disclosed as possessing angiotensin converting enzyme inhibition activity.

Gordon et al. in U.S. patent application Ser. No. 442,681 filed Nov. 18, 1982, now U.S. Pat. No. 4,499,079, disclose various carboxy and substituted carboxycycloalkylcarbonyl dipeptides. These compounds are disclosed as possessing angiotensin converting enzyme inhibition activity and depending upon the terminal α-amino acid also possessing enkephalinase inhibition activity.

Weller et al. in U.S. patent application Ser. No. 446,923 filed Dec. 6, 1982, now U.S. Pat. No. 4,456,595, disclose various carboxy and substituted carboxyarylcarbonyl dipeptides. These compounds are disclosed as possessing angiotensin converting enzyme inhibition activity and depending upon the terminal α-amino acid also possessing enkephalinase inhibition activity.

SUMMARY OF THE INVENTION

This invention is directed to the mercaptocycloalkylcarbonyl and mercaptoarylcarbonyl dipeptide compounds of formula I and salts thereof (I)

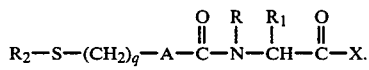

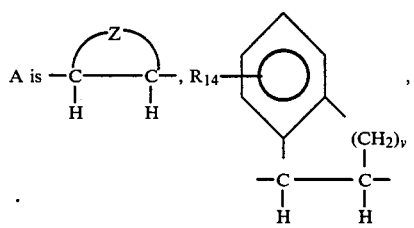

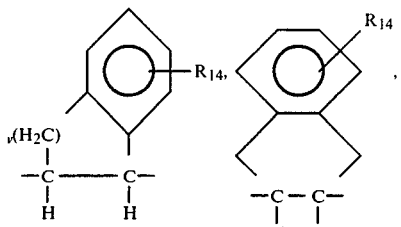

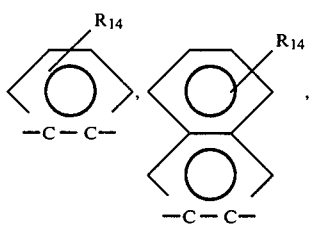

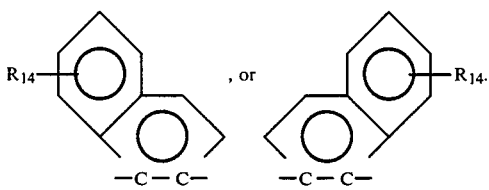

v is one or two.

Z completes a cycloalkyl ring of 3 to 10 carbons; said cycloalkyl ring in which one of the carbon atoms is substituted by a lower alkyl of 1 to 4 carbons, lower alkoxy of 1 to 4 carbons, lower alkylthio of 1 to 4 carbons, phenyl, benzyl, halo, trifluoromethyl, or hydroxy group; or a cycloalkenyl ring of 5 to 7 carbons.

X is an amino or imino acid of the formula

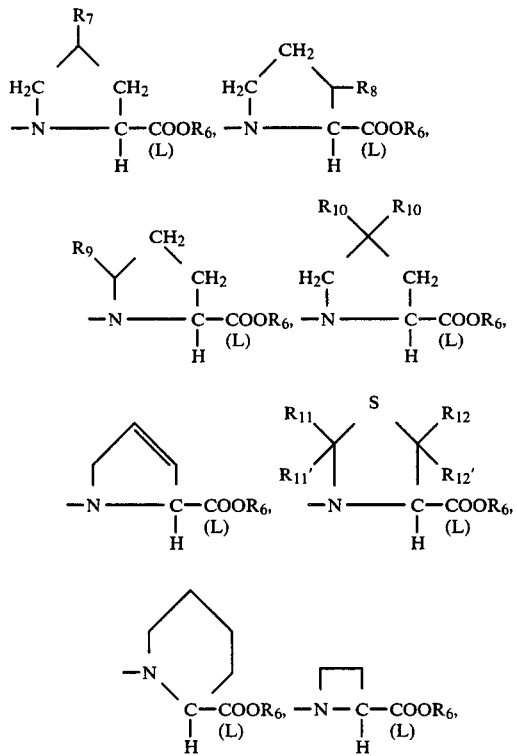

-continued
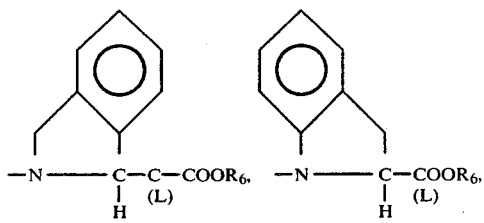
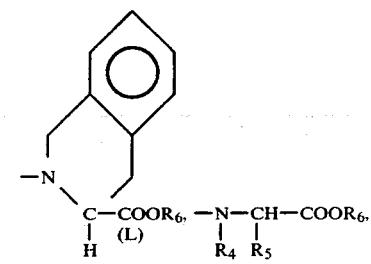
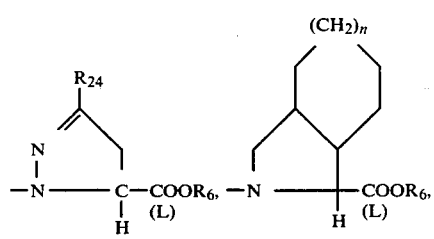
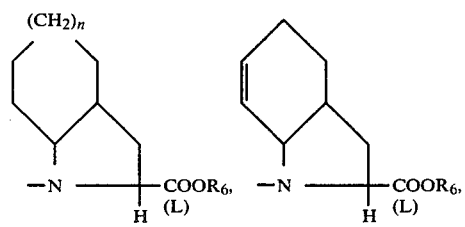
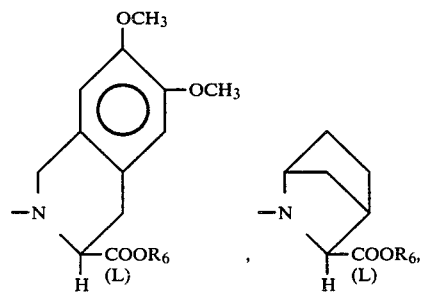
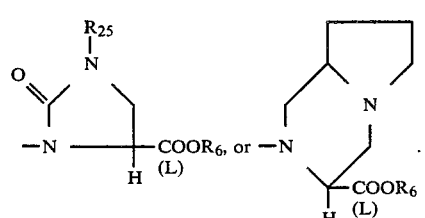
n is zero, one, or two.
R₂₅ is lower alkyl of 1 to 4 carbons or
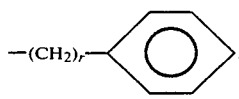
R₇ is
hydrogen, lower alkyl, halogen, hydroxy,
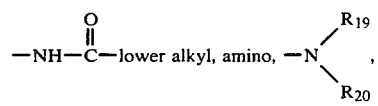
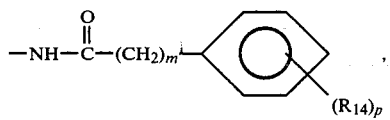
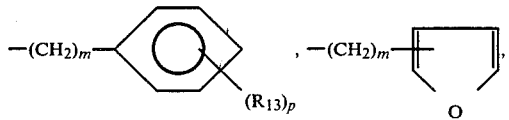
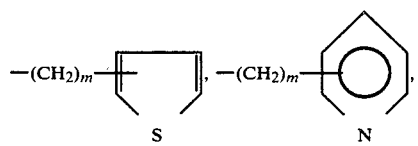
a 1- or 2-naphthyl of the formula
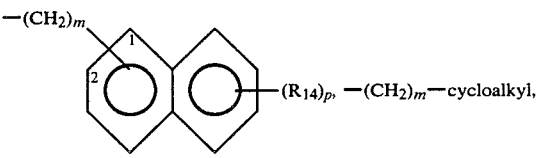
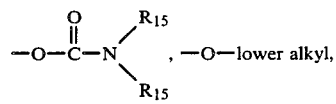
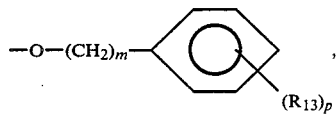
a 1- or 2-naphthyloxy of the formula
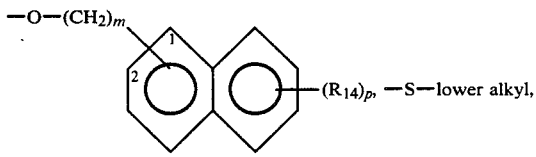
, or a 1- or 2-naphthylthio -continued of the formula —S—$(CH_2)_m$— 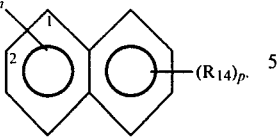

$R_8$ is halogen, 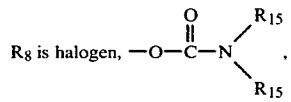,

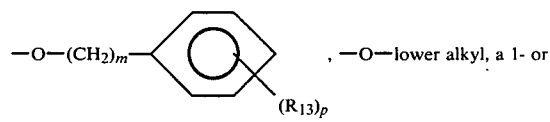, —O—lower alkyl, a 1- or 2-naphthyloxy of the formula

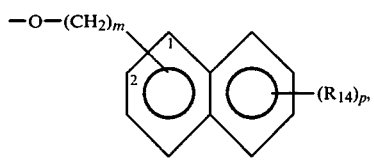

—S—lower alkyl, 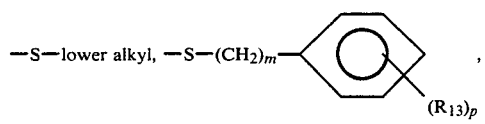, or a 1- or 2-naphthylthio of the formula

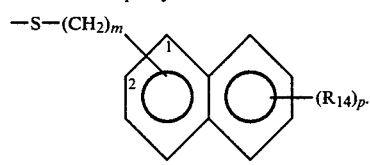

$R_9$ is keto or 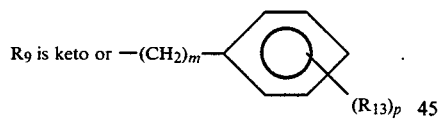.

$R_{10}$ is halogen or —Y—$R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

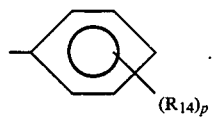

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

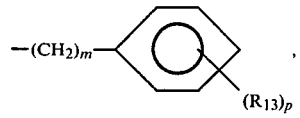, or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is

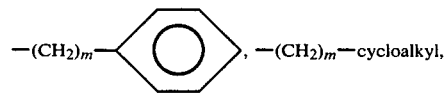

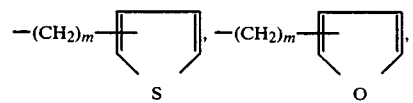

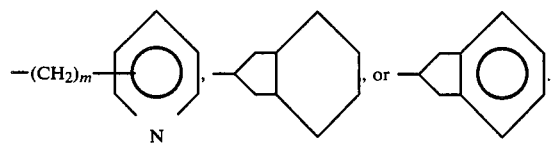

$R_5$ is hydrogen, lower alkyl, 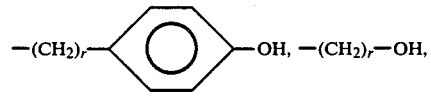,

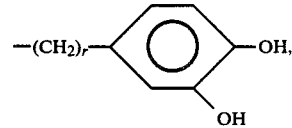

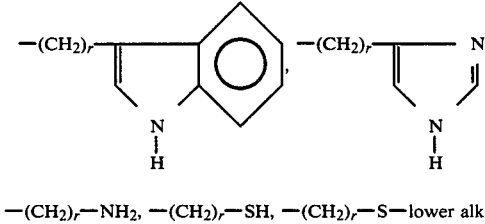

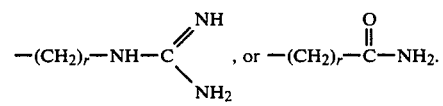

r is an integer from 1 to 4.

$R_{19}$ is lower alkyl, benzyl, or phenethyl.
$R_{20}$ is hydrogen, lower alkyl, benzyl or phenethyl.
R is hydrogen, lower alkyl, cycloalkyl,

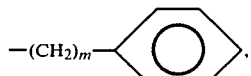

$-(CH_2)_2-NH_2$, $-(CH_2)_3-NH_2$, $-(CH_2)_4-NH_2$, $-(CH_2)_2-OH$, $-(CH_2)_3-OH$, $-(CH_2)_4-OH$, $-(CH_2)_2-SH$, $-(CH_2)_3-SH$, or $-(CH_2)_4-SH$.

$R_1$ is hydrogen, lower alkyl, halo substituted lower alkyl,

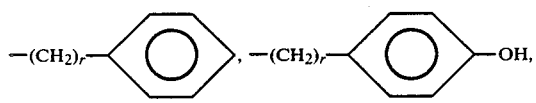

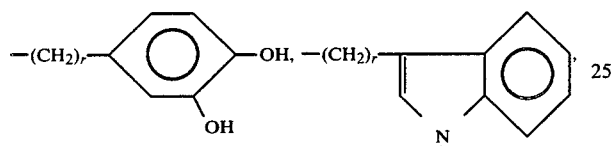

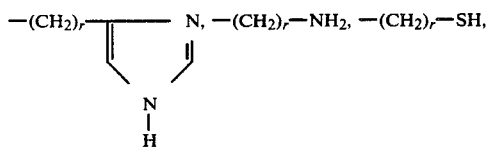 

—$(CH_2)_r$—OH, —$(CH_2)_r$—S—lower alkyl,

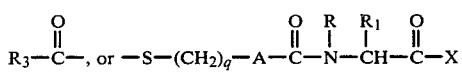

—$(CH_2)_r$—C—NH$_2$.

$R_2$ is hydrogen,

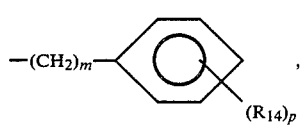

to form a symmetrical disulfide.
$R_3$ is lower alkyl,

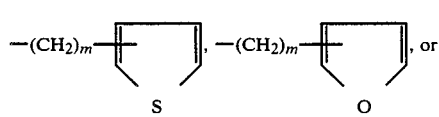

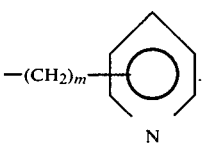

$R_6$ is hydrogen, lower alkyl, benzyl, benzhydryl, a pharmaceutically acceptable salt ion,

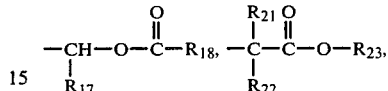

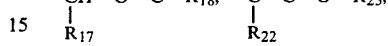

—CH—(CH$_2$—OH)$_2$, —CH$_2$—CH—CH$_2$,
      |        |
      OH       OH

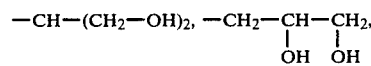

—$(CH_2)_2$—N(CH$_3$)$_2$ or $R_{17}$ is hydrogen, lower alkyl, cycloalkyl, or phenyl.
$R_{18}$ is hydrogen, lower alkyl, lower alkoxy or phenyl or $R_{17}$ and $R_{18}$ taken together are —(CH$_2$)$_2$—, —(CH$_2$)$_3$—, —CH=CH—, or

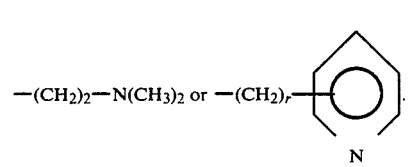

$R_{21}$ and $R_{22}$ are independently selected from hydrogen and lower alkyl.
$R_{23}$ is lower alkyl.
$R_{24}$ is hydrogen, lower alkyl,

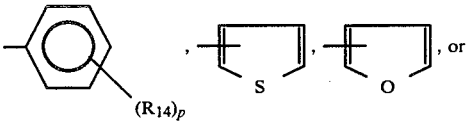

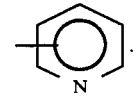

q is zero or one.

DETAILED DESCRIPTION OF THE INVENTION

This invention in its broadest aspects relates to the mercaptocycloalkylcarbonyl and mercaptoarylcarbonyl dipeptide compounds of formula I above, to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl group attached to an oxygen or sulfur.

The term cycloalkyl refers to saturated rings of 3 to 10 carbon atoms with cyclopentyl, cyclohexyl, and cycloheptyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols $$-(CH_2)_m\!-\!\!\left\langle\!\!\begin{array}{c}\\S\end{array}\!\!\right\rangle,\ -(CH_2)_m\!-\!\!\left\langle\!\!\begin{array}{c}\\O\end{array}\!\!\right\rangle,\ \text{and}$$

$$-(CH_2)_m\!-\!\!\left\langle\!\!\begin{array}{c}\\N\end{array}\!\!\right\rangle$$

represent that the alkylene bridge is attached to an available carbon atom.

The compounds of formula I wherein A is a cycloalkyl or substituted cycloalkyl ring of the formula $$-\underset{H}{\overset{Z}{C}}\!-\!\underset{H}{\overset{}{C}}\!-,\ R^{14}\!-\!\!\left\langle\!\!\begin{array}{c}\\(CH_2)_y\\-\underset{H}{\overset{}{C}}\!-\!\underset{H}{\overset{}{C}}\!-\end{array}\!\!\right\rangle,$$

$$\underset{y(H_2C)}{\!-\!\!\left\langle\!\!\begin{array}{c}\\-R_{14},\\-\underset{H}{\overset{}{C}}\!-\!\underset{H}{\overset{}{C}}\!-\end{array}\!\!\right\rangle}\text{ or }\underset{}{\!\!\left\langle\!\!\begin{array}{c}R_{14}\\\\-C\!-\!C\!-\\H\ H\end{array}\!\!\right\rangle},$$

q is zero, and $R_2$ is hydrogen can be prepared by coupling a protected mercaptocycloalkylcarboxylic acid of the formula $$\text{prot}-S-A-\overset{O}{\underset{\|}{C}}-OH \quad\quad (II)$$

wherein prot is a protecting group such as p-methoxybenzyl with a dipeptide ester of the formula $$HN-\overset{R}{\underset{|}{C}}H-\overset{R_1}{\underset{|}{C}}-\overset{O}{\underset{\|}{C}}-X \quad\quad (III)$$

wherein $R_6$ in the definition of X is an acid cleavable protecting group such as t-butyl, trimethylsilylethyl, benzhydryl, or p-methoxybenzyl. This reaction is preferably performed in the presence of a coupling agent such as dicyclohexylcarbodiimide or the like, or by conversion of the acid of formula II to its mixed anhydride, symmetrical anhydride, acid halide, active ester or by use of Woodward reagent K, N-ethoxycarbonyl-2-ethoxy-1,2-dihydroquinoline or the like. For a review of the methods of acylation see Methoden der Organischen Chemie (Houben-Weyl), Vol. XV, part II, page 1 et seq. (1974).

The resulting protected compound of the formula $$\text{prot}-S-A-\overset{O}{\underset{\|}{C}}-\overset{R}{\underset{|}{N}}-\overset{R_1}{\underset{|}{C}}H-\overset{O}{\underset{\|}{C}}-X \quad\quad (IV)$$

is treated with trifluoroacetic acid and anisole to remove the $R_6$ ester group and mercuric trifluoroacetate to remove the p-methoxybenzyl sulfur protecting group and give the mercaptan product of formula I, i.e., $R_2$ and $R_6$ are hydrogen.

The compounds of formula I wherein A is a cycloalkyl or substituted cycloalkyl of the formula shown above, q is zero, and $R_2$ is $$R_3-\overset{O}{\underset{\|}{C}}-$$

can be prepared by acylating the corresponding mercaptan of formula I with an acid halide of the formula $$R_3-\overset{O}{\underset{\|}{C}}-\text{halo} \quad\quad (V)$$

wherein halo is Cl or Br.

Also, the compounds of formula I wherein A is a cycloalkyl or substitued cycloalkyl of the formula shown above, q is zero, and $R_2$ is $$R_3-\overset{O}{\underset{\|}{C}}-$$

can be prepared by coupling an acylmercaptocycloalkylcarboxylic acid of the formula $$R_3-\overset{O}{\underset{\|}{C}}-S-A-\overset{O}{\underset{\|}{C}}-OH \quad\quad (VI)$$

with a dipeptide ester of formula III as described above. Treatment with trifluoroacetic acid and anisole removes the $R_6$ ester group and gives the acylmercapto product of formula I, i.e., $R_2$ is $$R_3-\overset{O}{\underset{\|}{C}}-$$

and $R_6$ is hydrogen.

The compounds of formula I wherein A is cycloalkyl or substituted cycloalkyl of the formulas shown above, q is zero, and $R_2$ is hydrogen can also be prepared by treating the corresponding compound of formula I wherein $R_2$ is $$R_3-\overset{O}{\underset{\|}{C}}-$$

with ammonia or sodium hydroxide as described by Ondetti et al. in U.S. Pat. No. 4,105,776.

The protected mercaptocycloalkylcarboxylic acid of formula II can be prepared by reacting a cycloalkylenecarboxylic acid of the formula

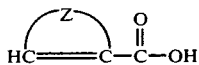
(VII)

or the formula

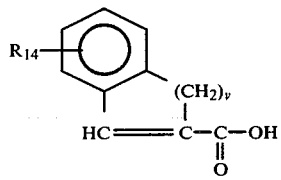
(VIII)

or the formula

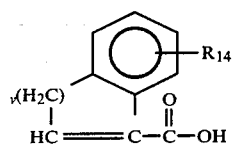
(IX)

or the formula

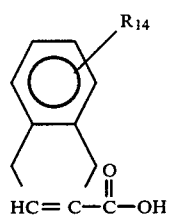
(X)

with a mercaptan of the formula (XI)

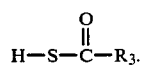

The acylmercaptocycloalkylcarboxylic acid of formula VI can be prepared by deprotecting the carboxylic acid of formula II followed by acylation with the acyl halide of formula V. Alternatively, the cycloalkylenecarboxylic acid of formulas VII, VIII, IX or X can be reacted with the mercaptan of the formula $$H-S-\overset{O}{\overset{\|}{C}}-R_3.$$
(XII)

The compounds of formula I wherein A is an aryl or substituted aryl ring of the formula

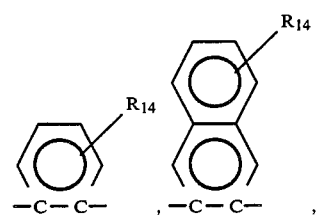

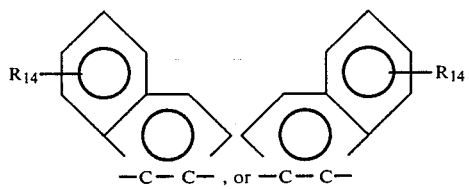

and $R_2$ is hydrogen can be prepared as follows. A disulfide arylcarboxylic or substituted arylcarboxylic acid of the formula

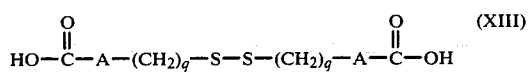
(XIII)

is coupled with the dipeptide ester of formula III to yield the arylcarbonyl or substituted arylcarbonyl disulfide ester product of formula I. Removal of the $R_6$ ester group yields the corresponding disulfide acid product. This coupling reaction is preferably performed in the presence of a coupling agent such as dicyclohexylcarbodiimide or by conversion of the acid of formula XIII to an activated form.

The arylcarbonyl or substituted arylcarbonyl disulfide compound is then treated with zinc in the presence of hydrochloric acid to yield the corresponding mercaptan product. Acylation of this mercaptan with the acyl halide of formula V yields the acylmercaptoarylcarbonyl or substituted arylcarbonyl dipeptides of formula I.

The compounds of formula I wherein q is one can be prepared by reacting a carboxylic acid cycloalkylcarbonyl or arylcarbonyl dipeptide of the formula

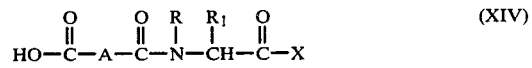
(XIV)

with borane in tetrahydrofuran to yield the corresponding alcohol of the formula

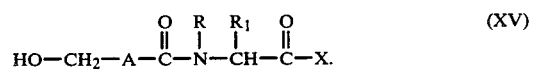
(XV)

The alcohol of formula XV is treated with the acylmercaptan of formula XII in the presence of diisopropylazodicarboxylate and triphenylphosphine to yield the products of formula I wherein $R_2$ is $$R_3-\overset{O}{\overset{\|}{C}}-$$

and q is one.

Treatment of this acrylmercapto product with sodium hydroxide or ammonia yields the corresponding mercaptan product, i.e., $R_2$ is hydrogen.

The carboxylic acid of formula XIV wherein A is cycloalkyl or substituted cycloalkyl are prepared as described by Gordon et al. in U.S. Ser. No. 442,681 filed Nov. 18, 1982. The carboxylic acid of formula XIV wherein A is aryl or substituted aryl are prepared as described by Weller et al. in U.S. Ser. No. 446,923 filed Dec. 6, 1982. As described in these applications, a carboxylic acid of the formula

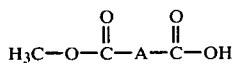

is coupled with a dipeptide of formula III to yield

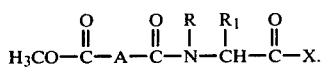

Treatment with sodium hydroxide yields the carboxylic acid of formula XIV.

The symmetrical disulfide compounds of formula I wherein $R_2$ is

can be prepared by direct oxidation of the corresponding mercaptan with iodine as taught by Ondetti et al. in U.S. Pat. No. 4,105,776.

The dipeptides of formula III are described in the literature. They can be obtained by reacting the N-protected amino acid of the formula

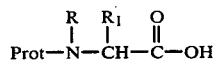 (XVII)

wherein the N-protecting group is benzyloxycarbonyl, t-butoxycarbonyl, or p-methoxybenzyloxycarbonyl with the imino or amino acid ester of the formula (XVIII)

Removal of the N-protecting group yields the intermediate of formula III. When the imino or amino acid of formula XVIII is known in the acid form it can be readily converted to the ester by conventional means. For example, the esters where $R_6$ is t-butyl can be obtained by treating the corresponding N-carbobenzyloxy imino or amino acid with isobutylene under acidic conditions and then removing the N-carbobenzyloxy protecting group by catalytic hydrogenation.

In the above reactions if any or all of R, $R_1$ and $R_5$ are

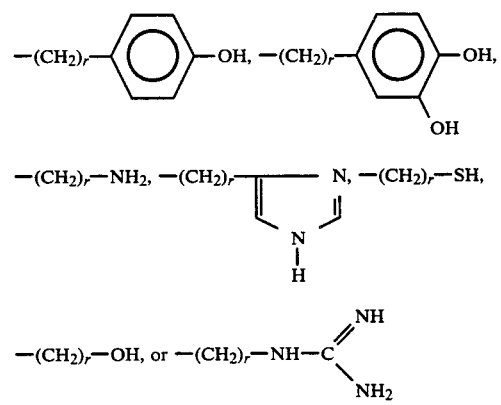

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is

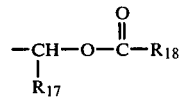

may be obtained by employing the dipeptide of formula III in the above reactions with such ester group already in place. Such ester reactants can be prepared by treating the dipeptide of formula III wherein $R_6$ is hydrogen with an acid chloride such as

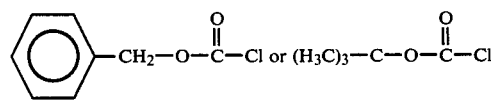

so as to protect the N-atom. The protected compound is then reacted in the presence of a base with a compound of formula

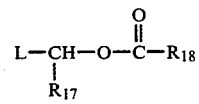 (XIX)

wherein L is a leaving group such as chlorine, bromine, tolylsulfonyl, etc., followed by removal of the N-protecting group such as by treatment with acid or hydrogenation.

The ester products of formula I wherein $R_6$ is

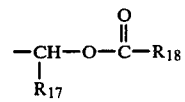

can also be obtained by treating the product of formula I wherein $R_6$ is hydrogen with a molar excess of the compound of formula XIX.

The ester products of formula I wherein $R_6$ is

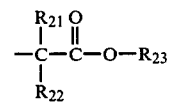

can be prepared by treating the product of formula I wherein $R_6$ is hydrogen with a molar excess of the compound of the formula

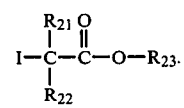 (XX)

The ester products of formula I wherein $R_6$ is $-CH-(CH_2-OH)_2$ or

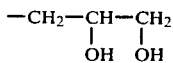

can be prepared by coupling the product of formula I wherein $R_6$ is hydrogen with a molar excess of the compound of the formula

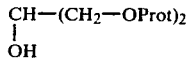
(XXI)

or the formula

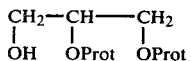
(XXII)

in the presence of a coupling agent such as dicyclohexylcarbodiimide followed by removal of the hydroxyl protecting groups.

Similarly, the ester products of formula I wherein $R_6$ is $-(CH_2)_2-N(CH_3)_2$ or

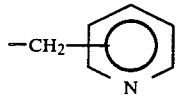

can be prepared by coupling the product of formula I wherein $R_6$ is hydrogen with a molar excess of the compound of the formula (XXIII)

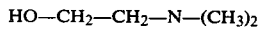

or the formula

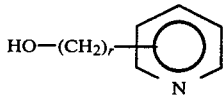
(XXIV)

in the presence of a coupling agent such as dicyclohexylcarbodiimide and the optional presence of a catalyst such as 4-dimethylaminopyridine.

The products of formula I wherein $R_7$ is amino may be obtained by reducing the corresponding products of formula I wherein $R_7$ is azido.

Preferred compounds of this invention with respect to the peptide part of the structure of formula I are those wherein:

R is hydrogen or straight or branched chain lower alkyl of 1 to 4 carbons.

$R_1$ is hydrogen, straight or branched chain lower alkyl or 1 to 4 carbons, $-CF_3$, $-(CH_2)_r-NH_2$ wherein r is an integer from 1 to 4,

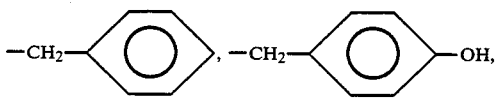

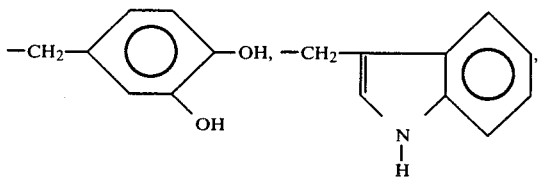

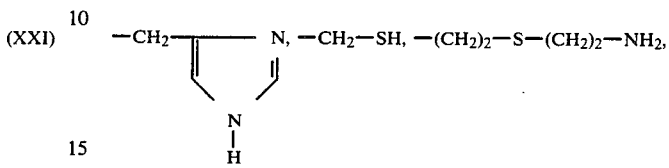

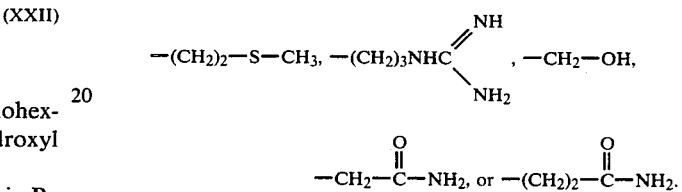

$R_4$ is hydrogen, cyclohexyl or phenyl.

$R_5$ is hydrogen, straight or branched chain lower alkyl of 1 to 4 carbons, $-CH_2OH$,

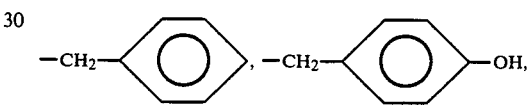

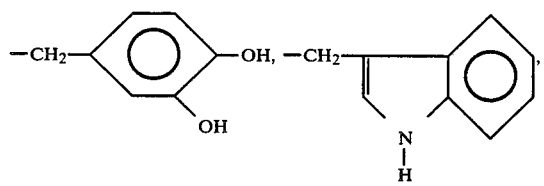

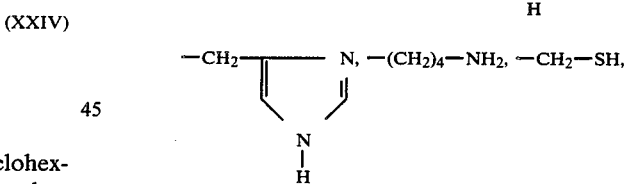

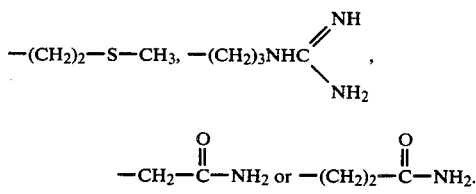

$R_6$ is hydrogen, straight or branched chain lower alkyl of 1 to 4 carbons, alkali metal salt,

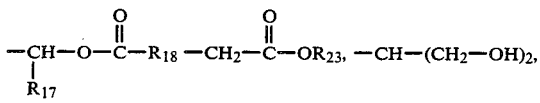

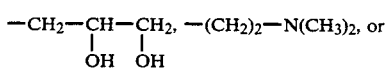

-continued

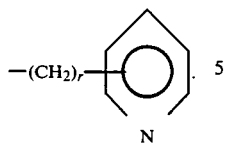

r is an integer from 1 to 4.

$R_{23}$ is straight or branched chain lower alkyl of 1 to 4 carbons, especially —C(CH$_3$)$_3$.

$R_{17}$ is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

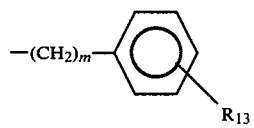

wherein m is zero, one or two and $R_{13}$ is hydrogen, methyl, methoxy, methylthio, chloro, bromo, fluoro, or hydroxy.

$R_7$ is

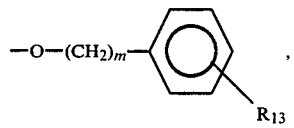

1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

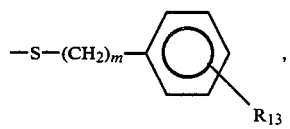

1-naphthylthio, or 2-naphthylthio wherein m is zero, one, or two and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

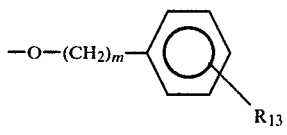

wherein m is zero, one, or two and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

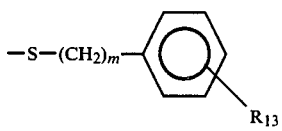

wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R'_{11}$, $R_{12}$ and $R'_{12}$ are all hydrogen, or $R_{11}$ is phenyl, 2-hydroxyphenyl, or 4-hydroxyphenyl and $R'_{11}$, $R_{12}$ and $R'_{12}$ are hydrogen.

$R_{24}$ is phenyl.

Most preferred compounds of this invention with respect to the peptide part of the structure of formula I are those wherein:

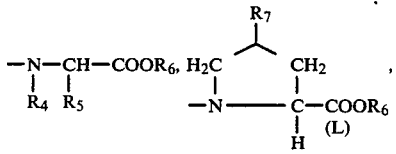

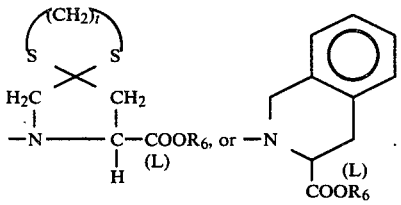

R is hydrogen or methyl.

$R_1$ is hydrogen, methyl, benzyl, or —(CH$_2$)$_4$—NH$_2$.

$R_6$ is hydrogen, straight or branched chain lower alkyl of 1 to 4 carbons, or an alkali metal salt.

$R_4$ is cyclohexyl or phenyl and $R_5$ is hydrogen.

$R_4$ is hydrogen and $R_5$ is methyl,

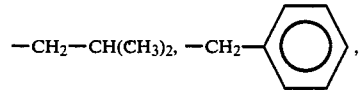

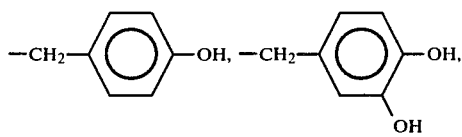

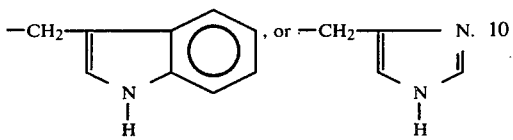

R₇ is hydrogen, cyclohexyl, lower alkoxy of 1 to 4 carbons,

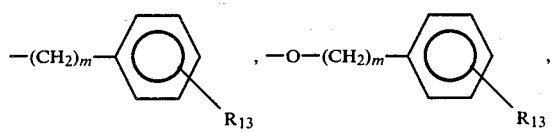

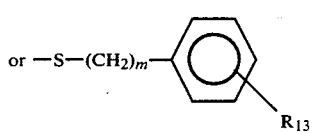

wherein m is zero, one, or two and R₁₃ is hydrogen, methyl, methoxy, methylthio, Cl, Br, F, or hydroxy, especially preferred wherein R₇ is hydrogen.

t is two or three, especially where t is two.

Preferred compounds of this invention with respect to the mercaptocycloalkylcarbonyl and mercaptoarylcarbonyl portion of the structure of formula I are those wherein:

A is

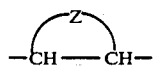

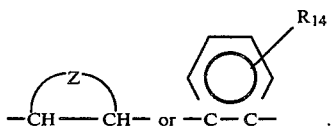

Z completes a cycloalkyl ring of 4 to 7 carbons or a cycloalkyl ring of 4 to 7 carbons wherein one of the carbons is substituted by a methyl, methoxy, methylthio, phenyl, benzyl, hydroxy, Cl, Br, F or hydroxy especially wherein Z completes a cyclohexyl ring.

R₁₄ is hydrogen, methyl, methoxy, methylthio, Cl, Br, F, or hydroxy.

R₂ is hydrogen,

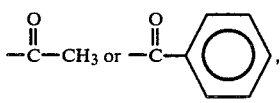

especially hydrogen.

The compounds of formula I wherein R₆ is hydrogen form salts with a variety of inorganic or organic bases. The nontoxic, pharmaceutically acceptable salts are preferred, although other salts are also useful in isolating or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Also, the compounds of formula I containing a free amino function form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

The peptide portion of the molecule of formula I when R₁ is other than hydrogen contains an asymmetric center. Preferably, this center will be in the L-configuration. When A is $$-\overset{\frown{\;\;Z\;\;}}{\underset{}{CH}}-\overset{}{\underset{}{CH}}-$$

the mercaptocycloalkylcarbonyl sidechain gives rise to cis-trans isomerism. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted also give rise to cis-trans isomerism. The configuration of the final product will depend upon the configuration of the R₇, R₈ and R₉ substituent in the starting material of formula XVIII.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

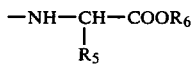

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade. HP-20 refers to a neutral polystyrene resin commercially available from Mitsubishi.

EXAMPLE 1

(trans)-1-[N-[(2-Mercaptocyclohexyl)carbonyl]-L-alanyl]-L-proline, monolithium salt (a)
(trans)-2-[[(4-Methoxyphenyl)methyl]thio]cyclohexanecarboxylic acid A solution of 1-cyclohexene carboxylic acid (22.1 g., 0.175 mole) and p-methoxy-α-toluenethiol (30.0 ml., 0.175 mole) in piperidine (55 ml.) is refluxed for 20 hours. The resulting solution is cooled, quenched with concentrated hydrochloric acid and diluted with ether. The mixture is filtered and the filtrate is washed with 1N hydrochloric acid (twice). The ether layer is concentrated and the residue is dissolved in hexane and extracted with 1N sodium hydroxide (twice). The combined aqueous layers are acidified with concentrated hydrochloric acid and extracted with ethyl acetate (twice). The extracts are dried (MgSO4) and concentrated to give 44.41 g. of 2-[[(4-methoxyphenyl)methyl]thio]cyclohexanecarboxylic acid as a clear oil. NMR analysis indicates a mixture of cis/trans isomers.

The above product is combined with material from a previous run (2.7 g.) and dissolved in ether. To this solution is added dicyclohexylamine (33.5 ml., 0.168 mole). The first crop of crystals is recrystallized from ethyl acetate to give 28.9 g. of (trans)-2-[[(4-methoxyphenyl)methyl]thio]-cyclohexanecarboxylic acid, dicyclohexylamine salt as a white solid; m.p. 147°–150°.

A portion of this dicyclohexylamine salt (10.5 g., 22.8 mmole) is dissolved in ethyl acetate and washed with 10% potassium bisulfate. The organic layer is dried and concentrated to give 6.4 g. of (trans)-2-[[(4methoxyphenyl)methyl]thio]cyclohexanecarboxylic as a crystalline solid. NMR analysis indicates all trans stereochemistry: 1H δ 2.40 (d,d,d; J=10,10,4 Hz) and 1H δ 2.75 (d,d,d; J=10, 10, 4 Hz).

(b)
(trans)-1-[N-[[[(4-Methoxyphenyl)methyl]thio]cyclohexylcarbonyl]-L-alanyl]-L-proline, 1,1-dimethylethyl ester A mixture of (trans)-2-[[(4-methoxyphenyl)methyl]thio]cyclohexanecarboxylic acid (2.0 g., 7.1 mmole), L-alanyl-L-proline, 1,1-dimethylethyl ester (1.7 g., 7.1 mmole), diisopropylethylamine (2.5 ml., 14.2 mmole), 1-hydroxybenzotriazole hydrate (0.96 g., 7.1 mmole) and dicyclohexylcarbodiimide (1.47 g., 7.1 mmole) in tetrahydrofuran (50 ml.) is stirred at room temperature for 15 hours. The mixture is filtered and the filtrate is diluted with ethyl acetate, washed with 1N hydrochloric acid, 10% sodium bicarbonate, saturated sodium chloride, dried (MgSO4), and concentrated to a white foam. The crude product is chromatographed on LPS-1 using an elution gradient of hexane:ethyl acetate (2:1→1:1). The product ($R_f$=0.65) is chromatographed a second time using a gradient of hexane:ethyl acetate (4:1→1:1). Fractions containing each of the isomers are combined and concentrated to give 0.5 g. of (trans)-1-[N-[[[(4-methoxyphenyl)methyl]thio]cyclohexylcarbonyl]-L-alanyl]-L-proline, 1,1-dimethylethyl ester (isomer A, fast running, $R_4$ 0.68), 0.28 g. of (trans)-1-[N-[[[(4-methoxyphenyl)methyl]thio]cyclohexylcarbonyl]-L-alanyl]-L-proline, 1,1-dimethylethyl ester (isomer B, slow running $R_f$ 0.63), and 1.46 g. of (trans)-1-[N-[[[(4-methoxyphenyl)methyl]thio]cyclohexylcarbonyl]-L-alanyl]-L-proline, 1,1-dimethylethyl ester (3:2 mixture of isomers B:A).

(c)
(trans)-1-[N-[(2-Mercaptocyclohexyl)carbonyl]-L-alanyl]-L-proline, monolithium salt A solution of trans-1-[N-[[[(4-methoxyphenyl)methyl]thio]cyclohexylcarbonyl]-L-alanyl]-L-proline, 1,1-dimethylethyl ester (3:2 mixture of isomers B:A) (0.37 g., 0.73 mmole) in trifluoroactic acuid (10 ml.) is stirred at room temperature for 2.5 hours. The solution is then cooled in an ice bath and mercuric acetate (0.233 g., 0.73 mmole) is added to the flask. The resulting solution is stirred at 0° for 20 minutes, concentrated, dissolved in toluene and concentrated to dryness. The residue is triturated with ether and the solid salt is collected.

Hydrogen sulfide is bubbled through a solution of the above salt in 80% acetic acid/water for 30 minutes. The resulting mixture is purged with argon and filtered. The filtrate is concentrated and filtered through silica gel (SilicAR CC-4) using 80% ethyl acetate:chloroform as eluant. The filtrate is concentrated and combined with material from a previous run (0.05 g.). The residue is treated with 1N lithium hydroxide (0.55 ml.), neutralized with AG50W×2 ion exchange resin (H+ form), filtered, washed with ether and lyophilized to give 0.094 g. of (trans)-1-[N-[(2-mercaptocyclohexyl)carbonyl]-L-alanyl]-L-proline, monolithium salt; m.p. 180°–200° (dec.); $[\alpha]_D^{25} = -68°$ (c=1% in methanol). TLC (silica gel; toluene:acetic acid, 4:1) $R_f$=0.24.

Anal. calc'd. for $C_{15}H_{23}N_2O_4SLi \cdot 1.75H_2O$: C,49.25; H, 7.30; N, 7.66; S, 8.76; SH, 9.04; Found: C,49.25; H, 7.05; N, 7.40; S, 8.37; SH, 8.86.

EXAMPLE 2

(trans)-1-[N-[(2-Mercaptocyclohexyl)carbonyl]-L-alanyl]-L-proline, monolithium salt (isomer A)

A solution of (trans)-1-[N-[[[(4-methoxyphenyl)methyl]thio]cyclohexylcarbonyl]-L-alanyl]-L-proline, 1,1-dimethylethyl ester (isomer A), from Example 1(b), (0.5 g., 0.99 mmole) in trifluoroacetic acid (10 ml.) is stirred at room temperature for 40 minutes and cooled to 0°. Mercuric acetate (0.32 g., 0.99 mmole) is added to the cold solution. The resulting solution is stirred at 0° for 15 minutes and concentrated. The residue is triturated with ether and the salt is collected.

Hydrogen sulfide is bubbled through a solution of the above salt in acetic acid for 30 minutes. The resulting solution is filtered through silica gel (SilicAR CC-4) using 80% ethyl acetate in chloroform as eluant. The filtrate is concentrated and treated with 1N lithium hydroxide and diluted with water. The solution is neutralized to pH 6 using AG50W×2 ion exchange resin (H+ form), filtered and lyophilized to give 0.11 g. of (trans)-1-[N-[(2-mercaptocyclohexyl)carbonyl]-L-alanyl]-L-proline, monolithium salt (isomer A); m.p. 200°–206° (dec.); $[\alpha]_D = -54°$ (c=0.8% in methanol). TLC (silica gel; toluene:acetic acid, 4:1) $R_f$=0.24.

Anal calc'd. for $C_{15}H_{23}N_2O_4SLi \cdot 1.5H_2O$: C, 49.85; H, 7.25; N, 7.75; S, 8.87; SH, 9.15; Found: C, 50.09; H, 7.24; N, 7.51; S, 8.58; SH, 9.26.

EXAMPLE 46

(trans)-1-[N-[(2-Mercaptocyclohexyl)carbonyl]-L-alanyl]-L-proline, monolithium salt (isomer B)

A solution of (trans)-1-[N-[[[(4-methoxyphenyl)methyl]thio]cyclohexylcarbonyl]-L-alanyl]-L-proline, 1,1-dimethylethyl ester (isomer B), from Example 1(b), (0.54 g., 1.07 mmole) in trifluoroacetic acid (10 ml.) is stirred at room temperature for 1.5 hours and cooled to 0°. Mercuric acetate (0.34 g., 1.07 mmole) is added to the cold solution. The resulting solution is stirred for 30 minutes and concentrated. The residue is triturated with ether and the solid salt is collected by filtration.

Hydrogen sulfide is bubbled through a solution of the above salt in acetic acid for 30 minutes at room temperature. The resulting mixture is filtered and concentrated. The product is chromatographed on silica gel (SilicAR CC-4) using a 20% to 100% ethyl acetate:chloroform gradient. The desired fractions are combined and concentrated. The residue is treated with 0.1M lithium carbonate (3 ml.), diluted with water and washed with ether. The aqueous solution is lyophilized to give 0.26 g. of (trans)-1-[N-[(2-mercaptocyclohexyl)carbonyl]-L-alanyl]-L-proline, monolithium salt (isomer B); m.p. 177° (dec.); $[\alpha]_D^{25} = -104°$ (c=1.0% in methanol). TLC (silica gel; toluene:acetic acid, 4:1) $R_f$=0.24.

Anal. calc'd. for $C_{15}H_{23}N_2O_4SLi \cdot 1.16H_2O$: C, 50.72; H, 7.09; N, 7.89; S, 9.03; SH, 9.31; Found: C, 50.72; H, 7.05; N, 7.81; S, 8.91; SH, 9.29.

EXAMPLE 4

N-[N-[(2-Mercaptocyclohexyl)carbonyl]-L-phenylalanyl]-L-leucine (a) 2-[[(4-Methoxyphenyl)methyl]thio]cyclohexanecarboxylic acid A solution of 1-cyclohexene carboxylic acid (2.75 g., 25 mmole) and p-methoxy-α-toluenethiol (3.62 ml., 26 mmole) in piperidine (6.5 ml.) is flushed with nitrogen and heated under reflux (drying tube) for 12 hours. The mixture is then acidified with concentrated hydrochloric acid (pH about 3), poured into ethyl ether (100 ml.), and filtered through Celite. The ether solution is washed with 0.5N hydrochloric acid, water, saturated sodium bicarbonate, and 5% potassium hydroxide (twice) (40 ml. each). The basic extracts are combined, washed with ethyl ether (40 ml.), acidified to pH of about 1 with concentrated hydrochloric acid, and again extracted with ethyl acetate (3×30 ml.). These organic extracts are washed with brine, dried ($Na_2SO_4$), and concentrated in vacuo to a light yellow oil (5.32 g.). This oil is applied to a column of 300 g. silica gel (230–400 mesh, E. Merck) and eluted with 9:1 cyclohexane:acetic acid. Fractions #33–51 (30 ml. each) are pooled and concentrated to give 4.63 g. of 2-[[(4-methoxyphenyl)methyl]thio]cyclohexanecarboxylic acid as a pale yellow, clear oil. TLC shows this material to be about a 2:3 mixture of cis-trans isomers.

(b) L-Phenylalanyl-L-leucine, 1,1-dimethylethyl ester, p-toluenesulfonic acid salt p-Toluenesulfonic acid (8.12 g., 42.7 mmole) is added to an ice-chilled solution of N-[N-[(phenylmethoxy)carbonyl]-L-phenylalanyl]-L-leucine, 1,1-dimethylethyl ester (20 g., 42.68 mmole) in 95% ethanol (325 ml.). The reaction vessel is purged with argon, and 10% palladium on carbon catalyst (2.0 g.) is added. The mixture is placed under 1 atmosphere of hydrogen and stirred for 20 hours. Filtering off the catalyst and concentrating the filtrate produces a sticky white solid which is triturated with ethyl ether and dried in vacuo to give 18.75 g. of L-phenylalanyl-L-leucine, 1,1-dimethylethyl ester, p-toluenesulfonic acid salt; m.p. (softens at 145°) 157°–159.5°.

(c) N-[N-[[[(4-Methoxyphenyl)methyl]thio]cyclohexylcarbonyl]-L-phenylalanyl]-L-leucine, 1,1-dimethylethyl ester A solution of dicyclohexylcarbodiimide (1.03 g., 5 mmole) in tetrahydrofuran (10 ml.) is added dropwise over 10 minutes to an ice chilled solution of L-phenylalanyl-L-leucine,1,1-dimethylethyl ester, p-toluenesulfonic acid salt (2.53 g., 5.0 mmole), 2-[[(4-methoxyphenyl)methyl]thio]cyclohexanecarboxylic acid (1.40 g., 5.0 mmole), from part (a), 1-hydroxybenzotriazole hydrate (0.68 g., 5 mmole), and diisopropylethylamine (1.74 ml., 10 mmole) in tetrahydrofuran (30 ml.) under nitrogen. The mixture is stirred overnight, warming to room temperature, and then diluted with ethyl ether (30 ml.). The dicyclohexylurea is removed by filtration and the residue is concentrated in vacuo. The oily residue is taken up in ethyl acetate (100 ml.), and washed with 10% potassium bisulfate (twice), saturated sodium bicarbonate, and 50% brine (30 ml. each), dried (Na$_2$SO$_4$), and concentrated in vacuo to an off-white foam. Chromatography on 180 g. of silica gel (230–400 mesh, E. Merck) eluting with 7:2 hexane:acetone yields a white foam that is recrystallized from hexane to give 2.22 g. of N-[N-[[[(4-methoxyphenyl)methyl]thio]cyclohexylcarbonyl]-L-phenylalanyl]-L-leucine, 1,1-dimethylethyl ester as a white solid; m.p. 69.5°–87°.

(d)
N-[N-[(2-Mercaptocyclohexyl)carbonyl]-L-phenylalanyl]-L-leucine

Prechilled (0°) trifluoroacetic acid (6 ml.) containing anisole (0.76 ml.) is added in one portion to N-[N-[[[(4-methoxyphenyl)methyl]thio]cyclohexylcarbonyl]-L-phenylalanyl]-L-leucine, 1,1-dimethylethyl ester (1.79 g., 3.0 mmole), from part (c). The mixture is stirred until all material is in solution, and cold (5°) trifluoromethanesulfonic acid (2.12 ml., 8 eq.) is added. The deep red solution is stirred for one hour in the cold, then toluene (10 ml.) is added and the trifluoroacetic acid is removed in vacuo. The residue is diluted with toluene (40 ml.) and cautiously poured into 60 ml. of ice water. The mixture is shaken and the resulting precipitate is filtered. The organic layer is separated, shaken with additional water (40 ml.), and again filtered. The combined solids are dried overnight over phosphorus pentoxide to yield a light pink powder that is recrystallized from ethyl acetate/hexane to give 0.77 g. of N-[N-[(2-mercaptocyclohexyl)carbonyl]-L-phenylalanyl]-L-leucine as a white solid; m.p. 168°–176°. TLC (silica gel, benzene:acetic acid, 9:1) R$_f$=0.30, 0.34.

Anal. calc'd. for C$_{22}$H$_{32}$N$_2$O$_4$S: C, 62.93; H, 7.67; N, 6.66; S, 7.62; SH, 100%; Found: C, 62.58; H, 7.63; N, 6.59; S, 7.49; SH, 101%.

EXAMPLE 5

N-[N-[(2-Mercaptocyclopentyl)carbonyl]-L-phenylalanyl]-L-leucine (pair A)

(a)
2-[[(Methoxyphenyl)methyl]thio]cyclopentanecarboxylic acid

A solution of 1-cyclopentene carboxylic acid (1.68 g., 15 mmole) and p-methoxy-α-toluenethiol (2.17 ml., 15.6 mmole) in piperidine (3.9 ml.) is flushed with argon and heated under reflux, protected by a drying tube, for 12 hours. The mixture is partitioned between ethyl ether (100 ml.) and 1N hydrochloric acid (3×40 ml.). The organic phase is stirred with activated charcoal (about 0.5 g.), dried (MgSO$_4$), filtered through Celite, and concentrated in vacuo to an orange-yellow oil. This oil is recrystallized successively (3 times) from cyclohexane/hexane to yield 1.75 g. of 2-[[(4-methoxyphenyl)methyl]thio]cyclopentanecarboxylic acid as a tan, granular solid; m.p. 63°–66°. TLC (silica gel, cyclohexane:acetic acid, 8:1) R$_f$=0.23.

(b) L-Phenylalanyl-L-leucine,1,1-dimethylethyl ester, hydrochloride

A solution of N-[N-[(phenylmethoxy)carbonyl]-L-phenylalanyl]-L-leucine, 1,1-dimethylethyl ester (93.72 g., 200.0 mmole) in 95% ethanol (1.5 l.) is hydrogenated under atmospheric pressure hydrogen using a 10% palladium on carbon (6.0 g.) catalyst. After stirring overnight, the mixture is filtered through Celite, concentrated to about ½ volume, filtered again, and concentrated to a viscous yellow oil. This oil is taken up in hexane (1.2 l.) and treated, with vigorous stirring, with 200 ml. of 1N hydrogen chloride in ether. The resulting thick, white suspension is diluted with hexane (1 l.), filtered, and washed with additional hexane. Drying overnight in vacuo over phosphorus pentoxide yields 71.80 g. of L-phenylalanyl-L-leucine, 1,1-dimethylethyl ester, hydrochloride as a white solid; m.p. 152.5°–154° with bubbling.

(c)
N-[N-[[[(4-Methoxyphenyl)methyl]thio]cyclopentylcarbonyl]-L-phenylalanyl]-L-leucine, 1,1-dimethylethyl ester A solution of dicyclohexylcarbodiimide (1.13 g., 5.48 mmole) in tetrahydrofuran (10 ml.) is added dropwise over 10 minutes to an ice/methanol chilled solution of L-phenylalanyl-L-leucine,1,1-dimethylethyl ester, hydrochloride (2.04 g., 5.0 mmole), 2-[[(4-methoxyphenyl)methyl]thio]cyclopentanecarboxylic acid (1.46 g., 5.48 mmole), hydroxybenzotriazole (0.74 g., 5.5 mmole) and diisopropylethylamine (1.40 ml., 8.04 mmole) in tetrahydrofuran (30 ml.). After stirring overnight, warming to room temperature, the mixture is filtered through Celite and concentrated in vacuo. The residue is taken up in ethyl acetate (60 ml.) and washed with saturated sodium bicarbonate, 50% brine, 10% potassium bisulfate (twice) and brine (30 ml. each), then dried (Na$_2$SO$_4$), and concentrated in vacuo to 3.13 g. of a light brown solid. A portion of this solid (2.59 g.) is chromatographed on a 150 g. column of silica gel (230–400 mesh, E. Merck), eluting with 7:2 hexane:acetone. Fractions containing the major product are pooled and concentrated to yield 2.14 g. of N-[N-[[[(4-methoxyphenyl)methyl]thio]cyclopentylcarbonyl]-L-phenylalanyl]-L-leucine, 1,1-dimethylethyl ester as a white solid; m.p. 126°–129.5°.

(e)
N-[N-[(2-Mercaptocyclopentyl)carbonyl]-L-phenylalanyl]-L-leucine (pair A)

Trifluoromethanesulfonic acid (1.77 ml., 20 mmole) is added in one portion to an ice-chilled solution of N-[N-[[[(4-methoxyphenyl)methyl]thio]cyclopentylcarbonyl]-L-phenylalanyl]-L-leucine,1,1-dimethylethyl ester (1.46., 2.51 mmole) is prechilled trifluoroacetic acid (5 ml.) and anisole (0.65 ml.). The dark red solution is stirred for 45 minutes in the cold, then it is diluted with toluene (60 ml.) and concentrated in vacuo to remove the trifluoroacetic acid. The residue is poured onto 100 g. of ice and water, and the solid precipitate is filtered to yield, after drying (CaSO$_4$), 1.10 g. of white solid. Recrystallization of the solid from benzene/hexane gives 0.682 g. of a pink, flocculent solid, which shows two spots by TLC (10% acetic acid/toluene). Chromatography of this solid on a 65 g. column of silica gel (230–400 mesh, E. Merck), eluting with 10% toluene/acetic acid gives 0.387 g. of the mixture of components and 87 mg. of the lower moving component.

A 0.19 g. portion of the mixed product is taken up in methanol (1.25 ml.) and treated, under argon, with 1N sodium hydroxide (1.5 ml.). The mixture is stirred for 3 hours at room temperature, then diluted with 30 ml. of water, washed with ethyl ether (20 ml.), and the aqueous layer is made acidic (pH about 1.5) with concentrated hydrochloric acid. The resulting precipitate is extracted with ethyl acetate (3×15 ml.). These extracts are washed with water and brine (15 ml. each), dried (Na$_2$SO$_4$), and concentrated in vacuo to yield 0.14 g. of a light brown solid. Recrystallization from ethyl acetate gives 119 mg. of N-[N-[(2-mercaptocyclopentyl)carbonyl]-L-phenylalanyl]-L-leucine (pair A) as a white, crystalline solid; m.p. 169.5°-172.5°. TLC (silica gel, benzene:acetic acid, 10:1) R$_f$=0.24 (with very faint tailing).

Anal. calc'd. for C$_{21}$H$_{30}$N$_2$O$_4$S: C, 62.04; H, 7.44; N, 6.89, S, 7.89; SH, 100%; Found: C, 61.81; H, 7.52; N, 6.89; S, 7.71; SH, 100%.

EXAMPLE 6

(trans)-N-[N-[(2-Mercaptocyclohexyl)carbonyl]-L-phenylalanyl]-L-leucine (isomer A)

(a)

(trans)-N-[N-[[[(4-Methoxyphenyl)methyl]thio]cyclohexylcarbonyl]-L-phenylalanyl]-L-leucine, 1,1-dimethylethyl ester (isomers A,B)

To a stirred solution of L-phenylalanyl-L-leucine, 1,1-dimethylethyl ester, hydrochloride (3.82 g., 10.3 mmole) in 75 ml. of tetrahydrofuran at 0°-5° under nitrogen is added diisopropylethylamine (2.15 ml., 12.36 mmole), (trans)-2-[[(4-methoxyphenyl)methyl]thio]cyclohexanecarboxylic acid (2.89 g., 10.3 mmole), from Example 1(a), and hydroxybenzotriazole hydrate (1.39 g., 10.3 mmole). A solution of dicyclohexylcarbodiimide (2.13 g., 10.3 mmole) in tetrahydrofuran (20 ml.) is added dropwise over 10 minutes. The ice-bath is removed and the reaction is allowed to stir overnight. The mixture is diluted with ethyl ether (60 ml.) and the dicyclohexylurea is filtered off. The filtrate is evaporated and the oily yellow residue is taken up in ethyl acetate (200 ml.). This solution is then washed sequentially with 10% potassium bisulfate, water, 5% sodium bicarbonate, water and brine (3×60 ml. each), then dried (Na$_2$SO$_4$), and concentrated in vacuo to yield 6.0 g. of a light yellow foam. This material is applied to a column of 400 g. of silica gel (230-400 mesh, E. Merck), eluting with a stepwise gradient of hexane/ethyl acetate (2:1 to 1:1). Two separate portions of material are isolated from this column, each enriched with one of the two isomers. Each portion is further purified by silica gel chromatography (twice, each). In a typical separation, approximately 2.5 g. of material is applied to a column of 175 g. of silica gel (230-400 mesh, E. Merck) eluting with toluene/acetone (15:1). The same column is used to separate the remaining portions of material. The combined yield of product is 4.25 g. in the following portions: 1.95 g. of (trans)-N-[N-[[[(4-methoxyphenyl)methyl]thio]cyclohexylcarbonyl]-L-phenylalanyl]-L-leucine,1,1-dimethylethyl ester (isomer A) as a white solid; m.p. 114°-115°; TLC (silica gel, toluene:acetone, 8:1) R$_f$=0.29; 1.11 g. of (trans)-N-[N-[[[(4-methoxyphenyl)methyl]thio]cyclohexylcarbonyl]-L-phenylalanyl]-L-leucine, 1,1-dimethylethyl ester (isomer B) as a white solid; m.p. 68°-70°; TLC (silica gel, toluene:acetone, 8:1) R$_f$=0.26; and 1.19 g. of a 2:1 mixture of isomers B:A.

(b)
(trans)-N-[N-[(2-Mercaptocyclohexyl)carbonyl]-L-phenylalanyl]-L-leucine (isomer A)

A solution of (trans)-N-[N-[[[(4-methoxyphenyl)methyl]thio]cyclohexylcarbonyl]-L-phenylalanyl]-L-leucine, 1,1-dimethylethyl ester (isomer A) (1.94 g., 3.25 mmole) in trifluoroacetic acid (50 ml.) is stirred at room temperature for 45 minutes. The solution is then cooled in an ice bath and mercuric acetate (1.04 g., 3.25 mmole) is added to the flask in one portion. The resulting deep violet solution is stirred at 0° for 20 minutes, then concentrated in vacuo. The residue is dissolved in toluene and concentrated in vacuo (twice), then triturated with ether to yield a light tan solid salt. This solid is dissolved in 80% acetic acid/water (50 ml.) and stirred while hydrogen sulfide is introduced for 20 minutes. The resulting black mixture is purged with argon and filtered through Celite. The filtrate is refiltered through a Teflon microfilter and concentrated in vacuo to yield 1.60 g. of a tan solid. This material is dissolved with heating in a small volume of toluene/acetic acid (9:1), applied to a column of 105 g. of silica gel (230-400 mesh, E. Merck) packed in toluene and eluted with toluene/acetic acid (9:1) to yield a colorless oil. This oil is dissolved in methanol and filtered through a cellulose microfilter to yield 1.27 g. of (trans)-N-[N-[(2-mercaptocyclohexyl)carbonyl]-L-phenylalanyl]-L-leucine (isomer A) as a white solid; m.p. 180°-183° (sinters above 85°); [α]$_D^{25}$ = −41.8° (c=1.10, methanol). TLC (silica gel, benzene:acetic acid, 4:1) R$_f$=0.47.

Anal. calc'd. for C$_{22}$H$_{32}$N$_2$O$_4$S 0.59H$_2$O: C, 61.29; H, 7.76; N, 6.50; S, 7.44; SH, 7.67; Found: C, 61.29; H, 7.51; N, 6.19; S, 7.39; SH, 7.66.

EXAMPLE 7

(trans)-N-[N-[(2-Mercaptocyclohexyl)carbonyl]-L-phenylalanyl]-L-leucine (isomer B)

A solution of (trans)-N-[N-[[[(4-methoxyphenyl)methyl]thio]cyclohexylcarbonyl]-L-phenylalanyl]-L-leucine,1,1-dimethylethyl ester (isomer B) (1.10 g., 1.84 mmole), from Example 6(a), in trifluoroacetic acid (30 ml.) is stirred at room temperature for 2 hours. The solution is then cooled in an ice bath and mercuric acetate (0.59 g., 1.84 mmole) is added to the flask in one portion. The resulting deep violet solution is stirred at 0° for 20 minutes, then concentrated in vacuo. The residue is dissolved in toluene and concentrated in vacuo (twice), then triturated with ether to yield a light tan solid salt. This solid is dissolved in 80% acetic acid/water (30 ml.) and stirred while hydrogen sulfide is introduced for 20 minutes. The resulting black mixture is purged with argon and filtered through Celite. The filtrate is refiltered through a Teflon microfilter and concentrated in vacuo. The residue is dissolved in ethyl acetate and the solution is concentrated in vacuo to yield 740 mg. of a white solid. This solid is recrystallized from ethyl acetate/hexane to yield 349 mg. of (trans)-N-[N-[(2-mercaptocyclohexyl)carbonyl]-L-phenylalanyl]-L-leucine (isomer B); m.p. 204°-206°; [α]$_D^{25}$ = −8.0° (c=0.87, methanol). TLC (silica gel, benzene:acetic acid, 4:1) R$_f$=0.40.

Anal. calc'd. for C$_{22}$H$_{32}$N$_2$O$_4$S.0.21H$_2$O: C, 62.27; H, 7.70; N, 6.60; S, 7.56; SH, 7.79; Found: C, 62.27; H, 7.57; N, 6.72; S, 7.53; SH, 7.83.

EXAMPLES 8-54

Following the procedure of Examples 1-7, the carboxylic acid shown below in Col. I is reacted with the thiol shown below in Col. II to yield the intermediate shown in Col. III. Coupling with the dipeptide shown in Col. IV yields the product shown in Col. V. Removal of the R$_6$ ester group and the S-protecting group yields the corresponding mercaptan product.

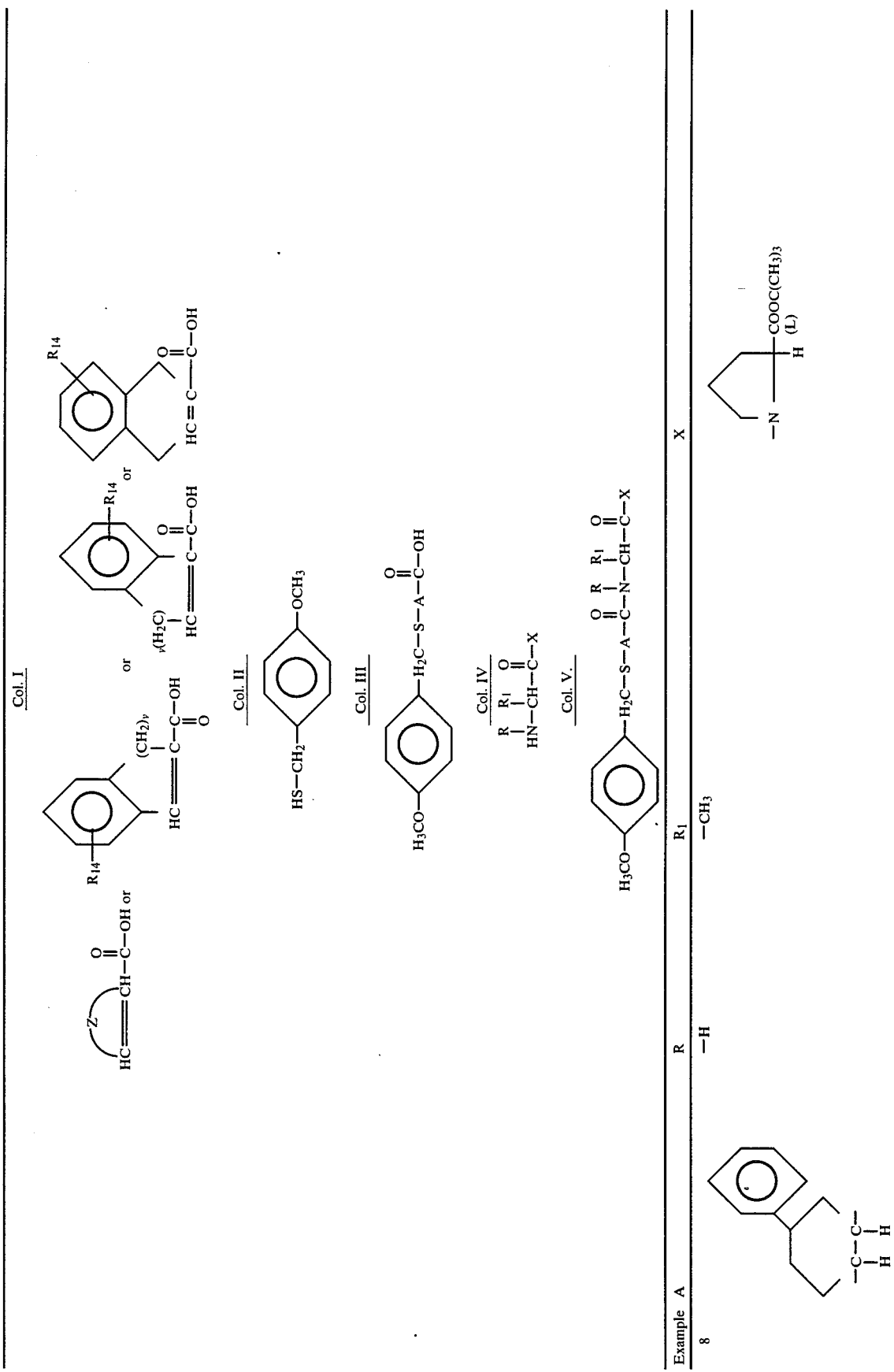

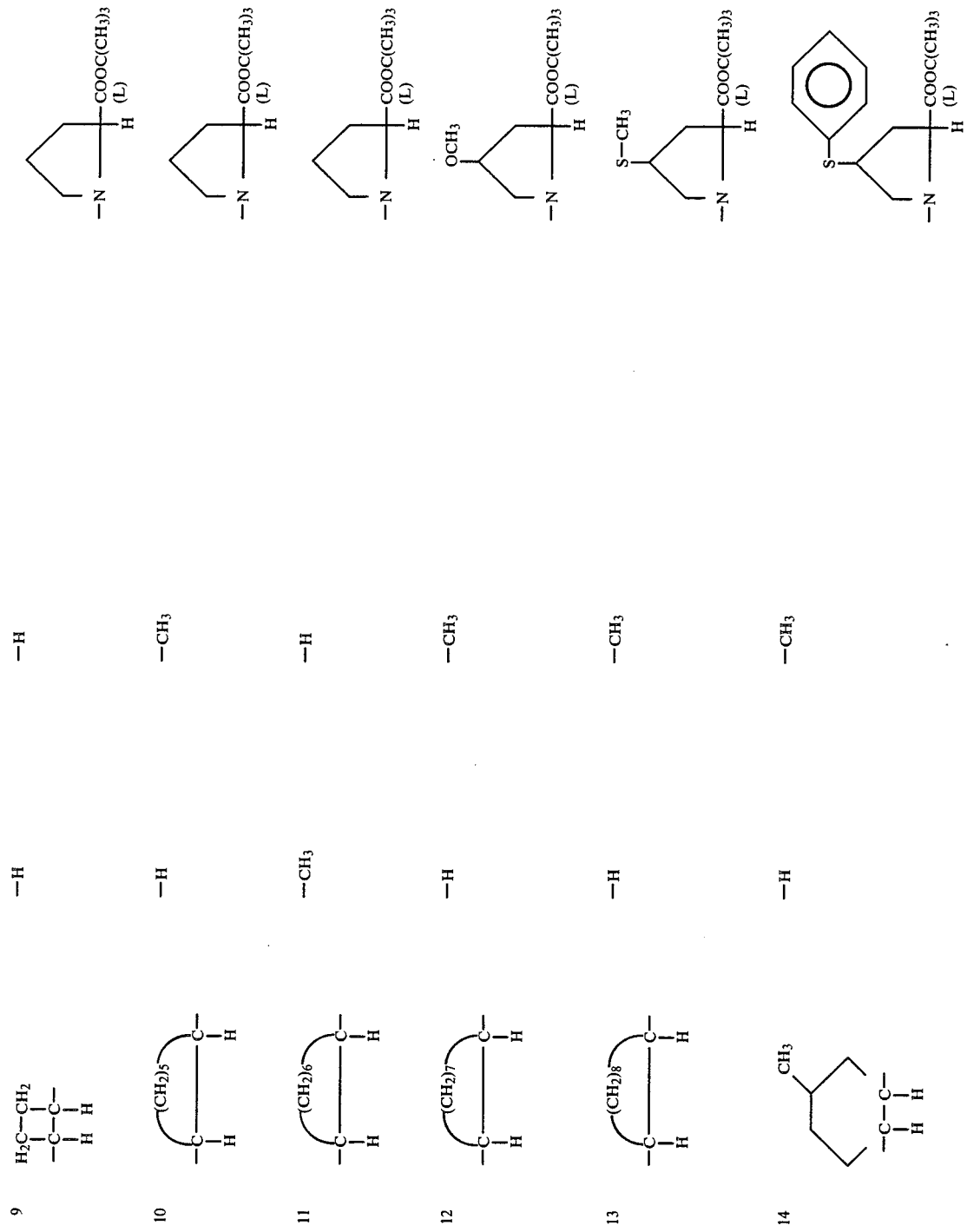

-continued
| | | | |
|---|---|---|---|
| 15 | 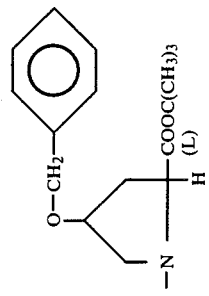 | —H | —CH$_3$ | 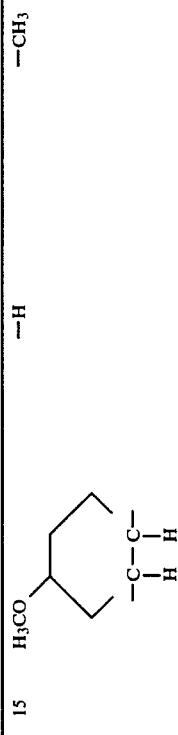 |
| 16 | 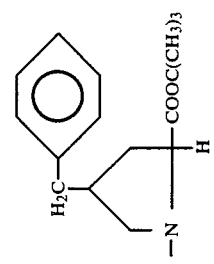 | —CH$_3$ | —H |  |
| 17 | 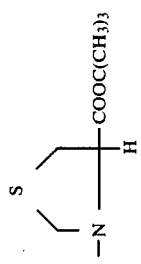 | —H | —H |  |
| 18 | | —H | —CH$_3$ | 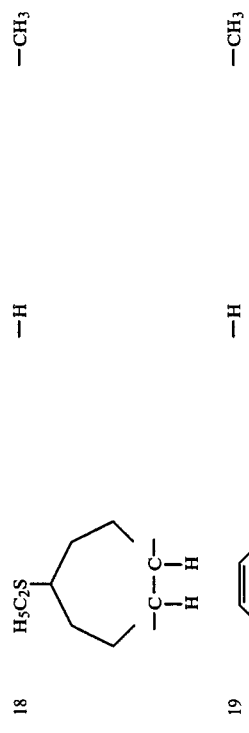 |
| 19 | 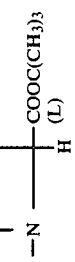 | —H | —CH$_3$ |  |

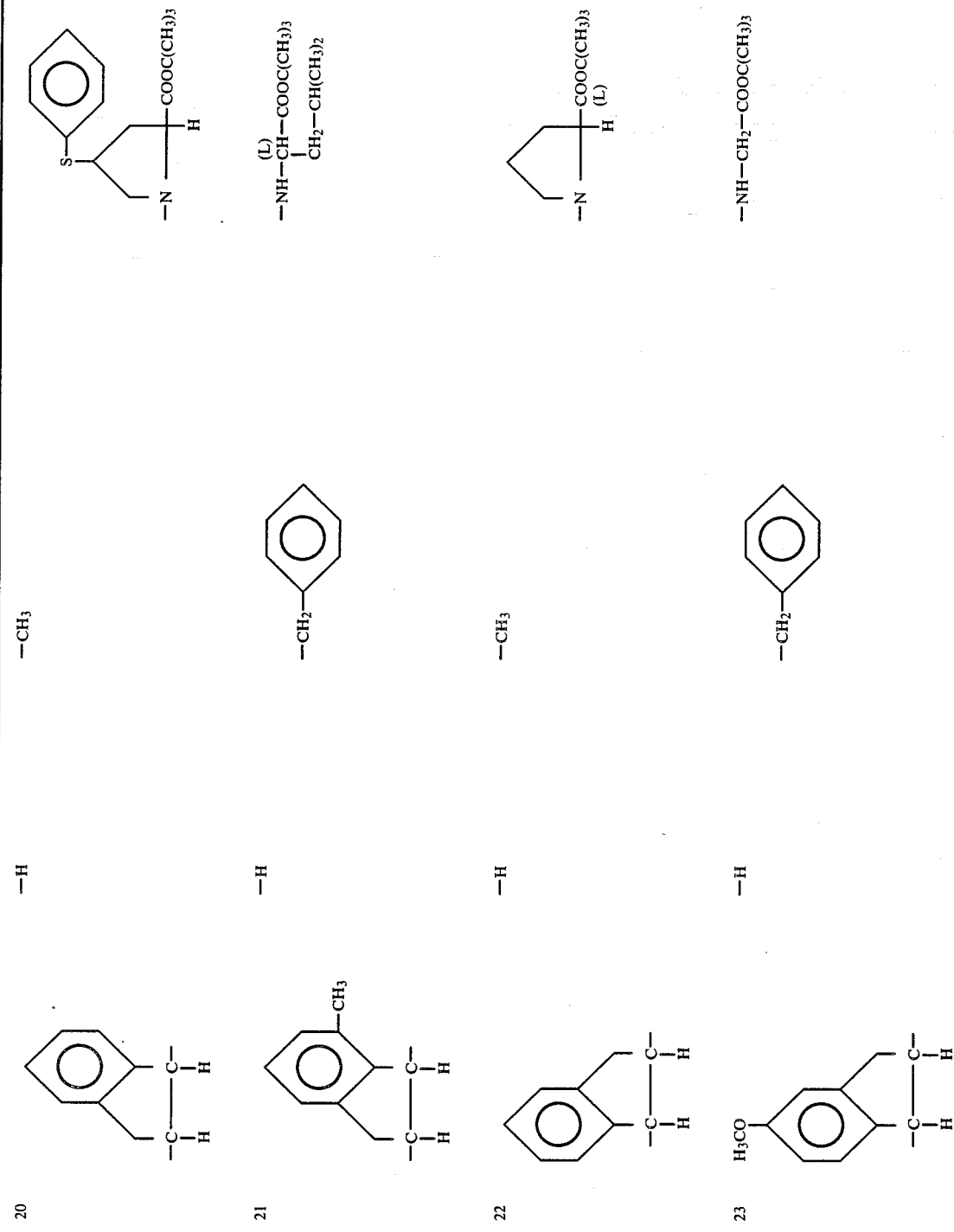

-continued
| | | | |
|---|---|---|---|
| 24 |  | —H | 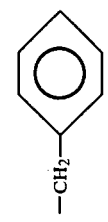 | —NH—CH(L)—COOC(CH₃)₃ / CH₂—CH(CH₃)₂ |
| 25 | 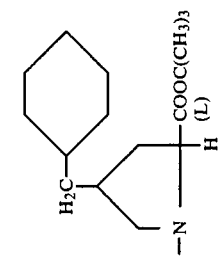 | —H | —CH₃ | 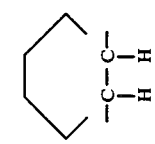 |
| 26 | 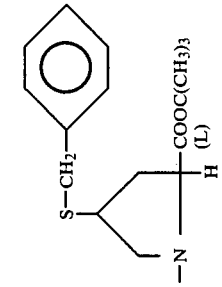 | —H | —CH₃ | 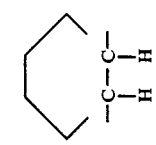 |
| 27 | 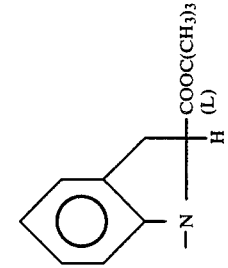 | —H | —CH₃ | 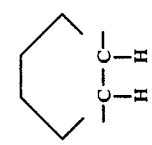 |

-continued
| | | | |
|---|---|---|---|
| 28 |  | —H | —CH₃ | 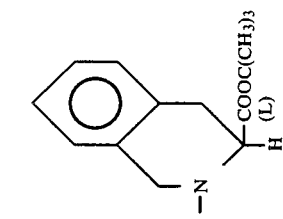 |
| 29 |  | —H | —CH₃ | 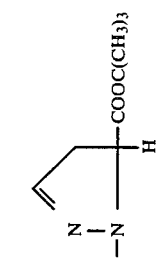 |
| 30 |  | —H | —CH₃ | 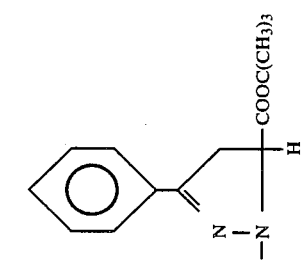 |
| 31 |  | —H | —CH₃ | |

-continued
| | | | |
|---|---|---|---|
| 32 |  | —H | —CH$_3$ | 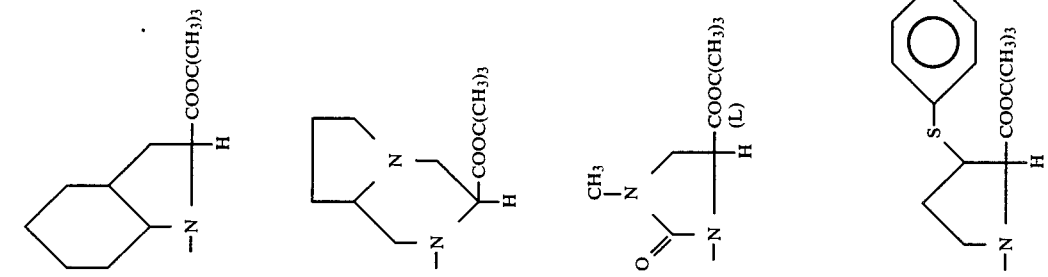 |
| 33 | | —H | —CH$_3$ | |
| 34 | 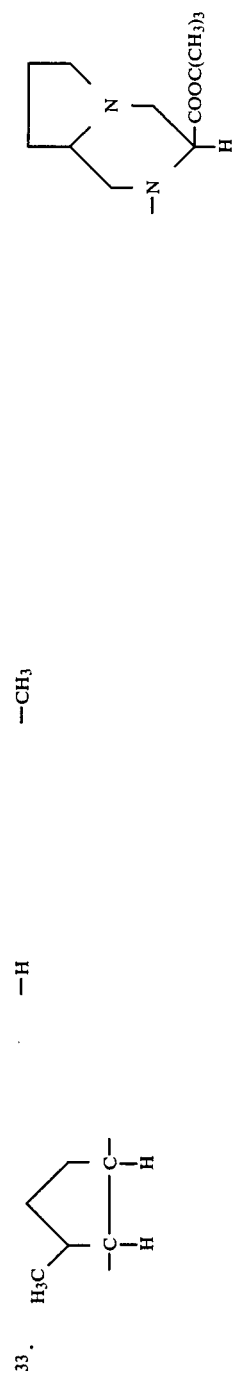 | —H | —CH$_3$ | 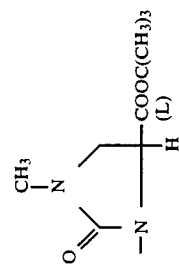 |
| 35 | 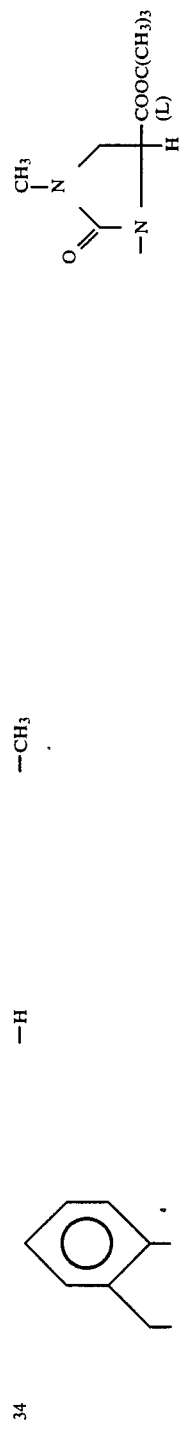 | —H | —(CH$_2$)$_3$—NH—C(=NH)—NH—NO$_2$ | 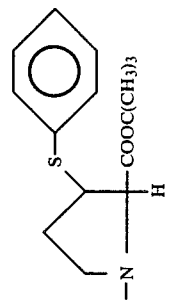 |
| | 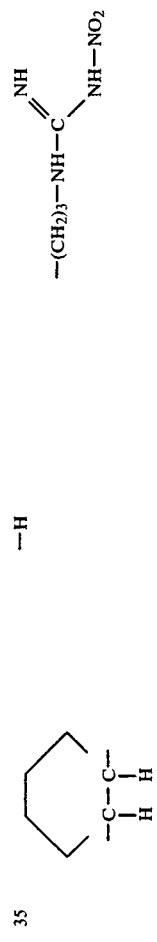 | | | |

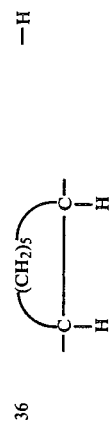
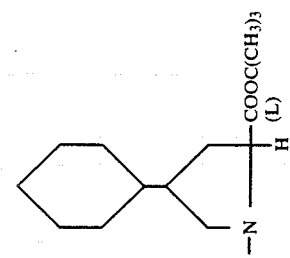
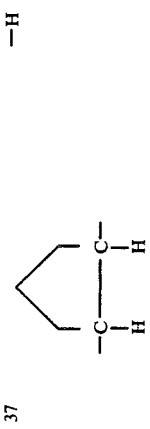
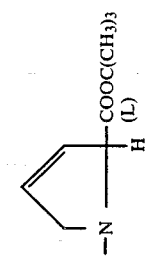
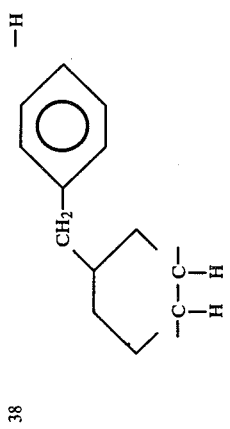
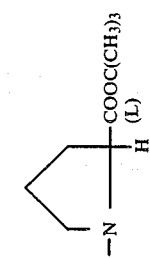
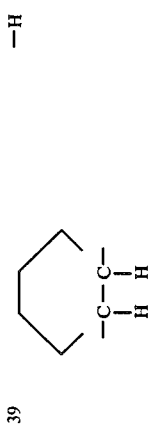
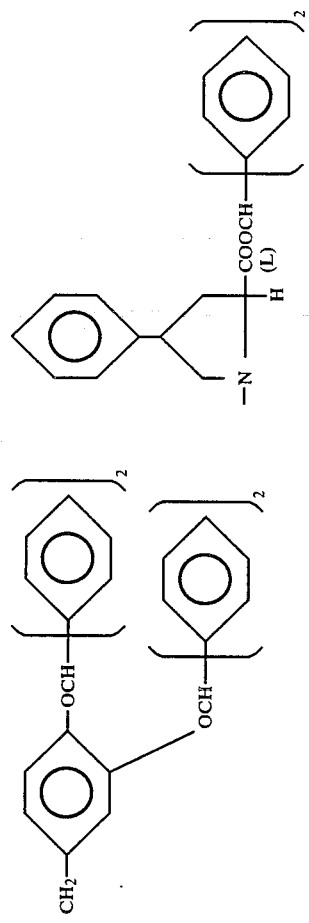

-continued
| | | | |
|---|---|---|---|
| 40 | 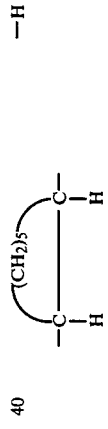 | —H | 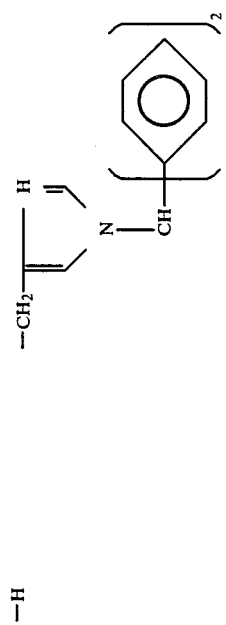 |
| 41 | | —H | |
| 42 | | —H | |
| 43 | | —CH₃ | |

-continued
| | | | |
|---|---|---|---|
| 49 | 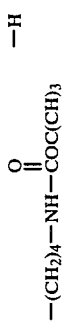 OCH₃ | —H | 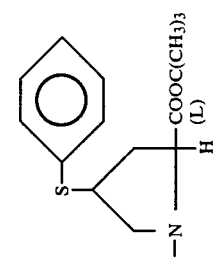 |
| 50 | 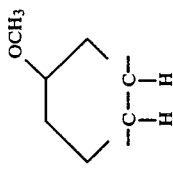 | —(CH₂)₄—NH—COC(CH)₃ (O) | 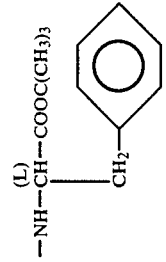 |
| 51 | 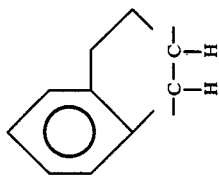 |  —CH₂— —CH₃ —H | 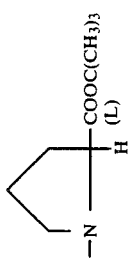 |
| 52 | 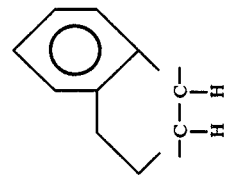 | —CH₃ —H | 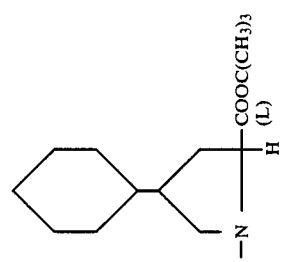 |

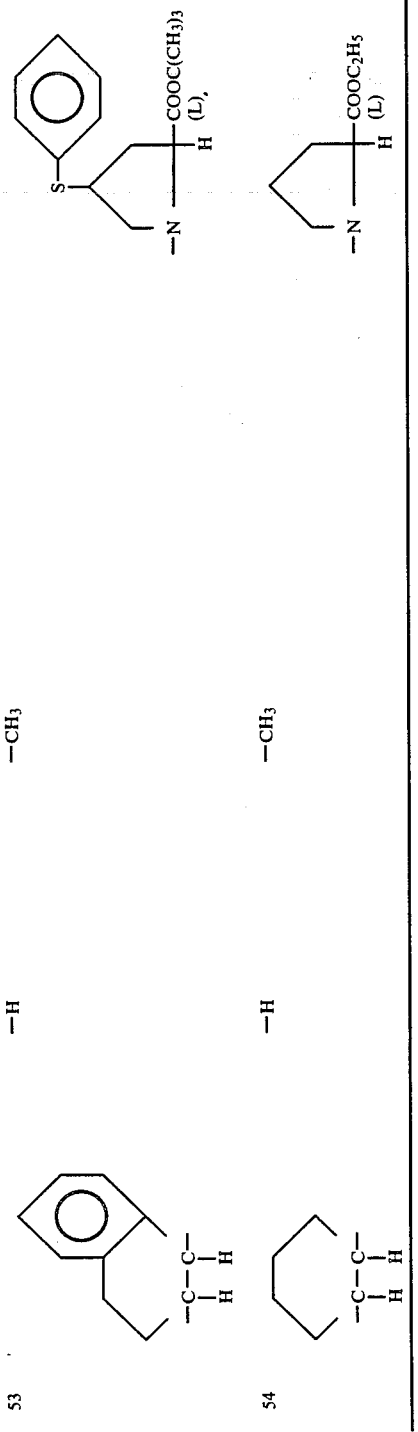

The R₁ protecting group in Examples 35 to 40, the R protecting group in Example 45, and the R₅ protecting groups in Examples 46 and 47 are removed as the last step in the synthesis. The 4-azidoproline of Example 41 when treated with a reducing agent yields a 4-aminoproline product.

EXAMPLE 55

N-[N-(2-Mercaptobenzoyl)-L-phenylalanyl]-L-leucine (a)

N,N'-(2,2'-Dithiobisbenzoyl)bis[L-phenylalanyl-L-leucine,1,1-dimethylethyl ester]

An argon flushed solution of L-phenylalanyl-L-leucine,1,1-dimethylethyl ester, p-toluenesulfonic acid salt (3.55 g., 7.0 mmole), prepared as described in Example 4(b), 1-hydroxybenzotriazole hydrate (0.95 g., 7.0 mmole), dicyclohexylcarbodiimide (1.44 g., 7.0 mmole), and diisopropylethylamine (1.83 ml., 10.5 mmole) in dimethylformamide (25 ml.) is placed under a drying tube and chilled to −5° (ice/methanol). A solution of 2,2'-dithiobisbenzoic acid (1.07 g., 3.50 mmole) in dimethylformamide (5 ml.) is added dropwise, followed by diisopropylethylamine (0.61 ml., 3.5 mmole) which is added in one portion. The mixture is stirred for 90 minutes in the cold, then the ice bath is removed and stirring continued for 24 hours. Ethyl acetate (50 ml.) is added to the resulting suspension, which is filtered from the dicyclohexyl urea and concentrated in vacuo to a brown gummy solid. This residue is taken up in ethyl acetate (60 ml.), and washed with water, saturated sodium bicarbonate, water, 10% pitassium bisulfate, and brine (30 ml. each), dried (Na₂SO₄), and concentrated in vacuo to a light brown foam. Chromatography on 200 g. of silica gel (230–400 mesh, E. Merck), eluting with hexane:acetone (5:2) yields 1.82 g. of N,N'-(2,2'-dithiobisbenzoyl)bis[L-phenylalanyl-L-leucine,1,1-dimethylethyl ester] as a white solid; m.p. 181°–184°.

(b)

N,N'-(2,2'-Dithiobisbenzoyl)bis[L-phenylalanyl-L-leucine]

N,N'-(2,2'-Dithiobisbenzoyl)bis[L-phenylalanyl-L-leucine, 1,1-dimethylethyl ester] (1.67 g., 1.78 mmole) is placed under an atmosphere of nitrogen and treated with 17.8 ml. of approximately 2N hydrogen chloride/acetic acid. The resulting solution is stirred for two hours at room temperature under a drying tube and then concentrated in vacuo. Toluene (30 ml.) is added to the oily yellow residue, which is again concentrated, and then treated with ethyl ether (50 ml.) and hexane (100 ml.). After standing overnight in the cold (refrigerator), the resulting yellow precipitate is filtered, triturated with hexane (twice), and dried in vacuo to give 1.25 g. of N,N'-(2,2'-dithiobisbenzoyl) bis[L-phenylalanyl-L-leucine] as a light yellow solid; m.p. 233°–235° (dec.).

(c)

N-[N-(2-Mercaptobenzoyl)-L-phenylalanyl]-L-leucine

A methanolic solution of N,N'-(2,2'-dithiobisbenzoyl)bis[L-phenylalanyl-L-leucine] (0.62 g., 0.75 mmole) (40 ml. of methanol) is chilled in an ice bath, and concentrated aqueous hydrochloric acid (6.43 ml.) is added, followed, over 30 minutes, by four portions of zinc dust (3.69 g. total). The residue is poured into 1N hydrochloric acid (150 ml.), and the resulting white precipitate is extracted with chloroform (3×25 ml.). The organic extracts are combined, washed with water (50 ml.), dried (Na₂SO₄), and concentrated to a slightly gummy residue (0.62 g.). Recrystallization from benzene (300 ml.) gives 0.40 g. of N-[N-(2-mercaptobenzoyl)-L-phenylalanyl]-L-leucine; m.p. shrinks at 117° melts at 127°–129°; $[\alpha]_D^{25} = -16.3°$ (c=1.0 in methanol). TLC (silica gel, benzene:acetic acid, 8:1) R$_f$=0.28.

Anal. calc'd. for C$_{22}$H$_{26}$N$_2$O$_4$S: C, 63.75; H, 6.32; N, 6.76; S, 7.74; SH, 100%; Found: C, 63.66; H, 6.26; N, 6.63; S, 7.88; SH, 102%.

EXAMPLES 56–64

Following the procedure of Example 55 but employing the dithiobisbenzoic acid shown below in Col. I one obtains the product shown in Col. II.

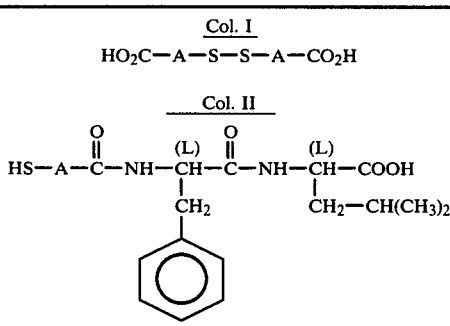

-continued

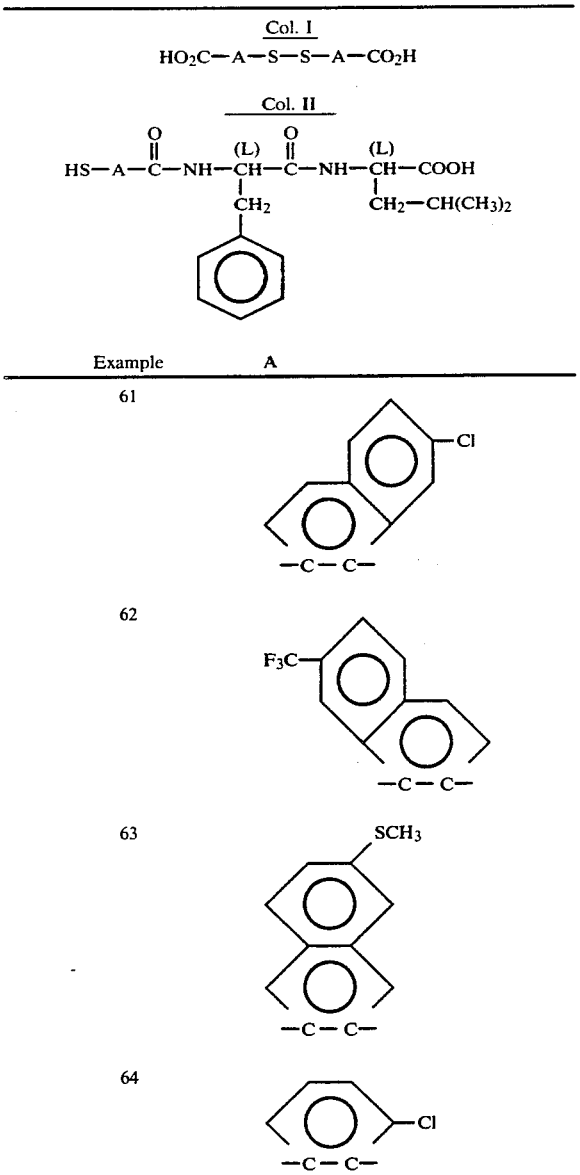

Also, the dipeptides of Examples 1 and 8 to 54 can be employed within the procedure of Examples 55 to 64 to give other products within the scope of the invention.

EXAMPLE 65

(trans)-N-[N-[[2-(Mercaptomethyl)cyclohexyl]carbonyl]-L-phenylalanyl]-L-leucine (a) (trans)-1,2-Cyclohexanedicarboxylic acid, mono(methyl)ester A suspension of (trans)-cyclohexane-1,2-dicarboxylic anhydride (38.54 g., 250.0 mmole) in methanol (55 ml.) is heated under reflux in a nitrogen atmosphere for 2 hours. The mixture is cooled, and concentrated in vacuo. After drying over phosphorus pentoxide, 46.12 g. of (trans)-1,2-cyclohexanedicarboxylic acid, mono(methyl)ester are obtained.

(b)
(trans)-N-[N-[2-[(Methoxycarbonyl)cyclohexyl]carbonyl]-L-phenylalanyl]-L-leucine,1,1-dimethylethyl ester A solution of dicyclohexylcarbodiimide (3.09 g., 15 mmole) in tetrahydrofuran (30 ml.) is added dropwise over 15 minutes to an ice/methanol chilled solution of L-phenylalanyl-L-leucine, 1,1-dimethylethyl ester, hydrochloride (5.58 g., 15.0 mmole), prepared as described in Example 5(b), (trans)-1,2-cyclohexanedicarboxylic acid, mono(methyl)ester (2.73 g., 15.0 mmole), hydroxybenzotriazole hydrate (2.04 g., 15.0 mmole) and diisopropylethylamine (3.93 ml., 22.6 mmole) in tetrahydrofuran (80 ml.). The mixture is stirred overnight under nitrogen, warming to room temperature, then filtered from the dicyclohexylurea (Celite) and concentrated in vacuo. The gummy residue is taken in ethyl acetate (80 ml.) and washed with 10% potassium bisulfate (twice), 50% brine, saturated sodium bicarbonate, 50% brine, and brine (50 ml. each), dried (MgSO$_4$), and concentrated to 6.96 g. of a yellow foam. Recrystallization from hexane yields 5.59 g. of (trans)-N-[N-[2-[(methoxycarbonyl)cyclohexyl]carbonyl]-L-phenylalanyl]-L-leucine, 1,1-dimethylethyl ester as an almost white solid.

(c)
(trans)-N-[N-[(2-Carboxycyclohexyl)carbonyl]-L-phenylalanyl]-L-leucine, 1,1-dimethylethyl ester A solution of (trans)-N-[N-[2-[(methoxycarbonyl)cyclohexyl]carbonyl]-L-phenylalanyl]-L-leucine,1,1-dimethylethyl ester (5.50 g., 10.9 mmole) in methanol (11 ml.) is treated, under argon, with 1N sodium hydroxide (12 ml.) over one hour. Additional methanol is added to maintain all material in solution, and the mixture is stirred for an additional four hours at room temperature. The methanol is removed in vacuo, and the residue is diluted with water (100 ml.). This solution is made acidic with concentrated hydrochloric acid (pH about 1), and extracted with ethyl acetate (3×40 ml.). The organic phases are combined, washed with water and brine (50 ml. each), dried (Na$_2$SO$_4$), and concentrated in vacuo to a foamy, light yellow solid. Attempted recrystallization from isopropyl ether/hexane yields a gum that is triturated with hexane to give 4.77 g. of (trans)/N-[N-[(2-carboxycyclohexyl)carbonyl]-L-phenylalanyl]-L-leucine,1,1-dimethylethyl ester as an off-white solid.

(d)
(trans)-N-[N-[[2-(Hydroxymethyl)cyclohexyl]carbonyl]-L-phenylalanyl]-L-leucine,1,1-dimethylethyl ester A solution of (trans)-N-[N-[(2-carboxycyclohexyl)carbonyl]-L-phenylalanyl]-L-leucine,1,1-dimethylethyl ester (4.50 g., 9.21 mmole) in tetrahydrofuran (10 ml.) is chilled, under argon, to −35° in carbon dioxide/acetone bath. To this solution is added, over 30 minutes, 0.96M borane-tetrahydrofuran complex (12 ml., 1.25 eq.). The mixture is stirred overnight, warming to 15°, then the excess borane is decomposed by careful addition of water (10 ml.). The tetrahydrofuran is removed in vacuo, and the residue is diluted with ethyl acetate (80 ml.), washed with saturated sodium bicarbonate, 10% potassium bisulfate, and brine (30 ml. each), then dried (Na$_2$SO$_4$), and concentrated to a yellow foam (3.38 g.). This material is purified chromatographically on the Waters model 500 preparative HPLC and, subsequently, on a column of 260 g. of silica gel (230–400 mesh, E. Merck), eluting with a 4.5% and 5% ethanol/cyclohexane, respectively, to yield 1.90 g. of (trans)-N-[N-[[2-(hydroxymethyl)cyclohexyl]carbonyl]-L-phenylalanyl]-L-leucine, 1,1-dimethylethyl ester as an off-white, foamy solid.

(e)

(trans)-N-[N-[[2-[(Acetylthio)methyl]cyclohexyl]carbonyl]-L-phenylalanyl]-L-leucine,1,1-dimethylethyl ester Diisopropylazodicarboxylate (0.20 ml., 1.0 mmole) is added to a cold (ice/methanol), well-stirred solution of triphenylphosphine (0.26 g., 1.0 mmole) in tetrahydrofuran (2.5 ml.) under nitrogen. Additional tetrahydrofuran (0.5 ml.) is added to thin the resulting slurry, and the mixture is stirred for 30 minutes in the cold. It is then treated, over seven minutes, with a solution of thiolacetic acid (76 mg., 1.0 mmole) and (trans)-N-[N-[[2-(hydroxymethyl)cyclohexyl]carbonyl]-L-phenylalanyl]-L-leucine, 1,1-dimethylethyl ester (0.47 g., 1.0 mmole) in tetrahydrofuran (1.5 ml.). The resulting black mixture is stirred for one hour in the cold, then one hour at room temperature, and the now light yellow solution is concentrated in vacuo. The oily residue is adsorbed onto a small amount of silica gel (230–400 mesh, E. Merck) and applied to a column of 80 g. of the same silica gel. Elution with hexane/acetone (11:2) yields 0.37 g. of (trans)-N-[N-[[2-[(acetylthio)methyl]cyclohexyl]carbonyl]-L-phenylalanyl]-L-leucine, 1,1-dimethylethyl ester. A second run obtains the desired product in greater purity as a white solid (fewer fractions are collected from the chromatography). Materials from the two runs are pooled.

(f)

(trans)-N-[N-[[2-[(Acetylthio)methyl]cyclohexyl]carbonyl]-L-phenylalanyl]-L-leucine, lithium salt (trans)-N-[N-[[2-[(Acetylthio)methyl]cyclohexyl]carbonyl]L-phenylalanyl]-L-leucine,1,1-dimethylethyl ester (0.50 g., 0.94 mmole) is treated, under nitrogen, with approximately 1.7N hydrogen chloride/acetic acid (5.5 ml.). The mixture is stirred for 6 hours at room temperature, after which time TLC shows presence of starting material. The solution is concentrated in vacuo and treated with additional hydrogen chloride/acetic acid as before. After 1.5 hours (reaction complete by TLC after one hour) the solution is concentrated. Toluene (7 ml.) is added to the residue, and removed in vacuo to yield a white solid. Chromatography of this material on 22 g. of silica gel (230–400 mesh, E. Merck) eluting with toluene/acetic acid (15:2) yields 0.30 g. of white solid. A portion of this solid is taken up in acetone (3 ml.) and treated with 0.44 ml. of 0.1M lithium carbonate. This solution is concentrated to about 1.5 ml., treated with sufficient methanol to solubilize the solids, and applied to 1 inch×13 inch column of HP-20. Elution with a linear water/acetonitrile gradient yields 38 mg. of (trans)-N-[N-[[2-[(acetylthio)methyl]cyclohexyl]carbonyl]-L-phenylalanyl]-L-leucine, lithium salt. The free acid is obtained by an acetonitrile wash of the column.

(g)

(trans)-N-[N-[[2-(Mercaptomethyl)cyclohexyl]carbonyl]-L-phenylalanyl]-L-leucine

A solution of the lithium salt product from part (f) (36 mg., 0.077 mmole) in methanol (0.3 ml.) is chilled (ice/methanol) under argon. 1N Sodium hydroxide (0.23 ml., 3 eq.) is added in one portion and the mixture is stirred for 75 minutes in the cold. The solvent is removed in vacuo, and the residue is treated with water (3 ml.) and concentrated hydrochloric acid (to pH about 1.5). The resulting white precipitate is extracted with ethyl acetate (3×15 ml.), and organic phases are combined, washed with water and brine (15 ml. each), dried (Na$_2$SO$_4$), and concentrated in vacuo. A white solid is obtained which is crystallized from benzene to yield 21 mg. of (trans)-N-[N-[[2-(mercaptomethyl)cyclohexyl]carbonyl]-L-phenylalanyl]-L-leucine as a flocculent, white solid; m.p. softens at 148°, melts at 156°–158°. TLC (silica gel, benzene:acetic acid, 8:1) R$_f$=0.41 with faint heading.

Anal. calc'd. for C$_{23}$H$_{34}$N$_2$O$_4$S.0.18H$_2$O: C, 63.09; H, 7.91; N, 6.40; S, 7.32; SH, 100%; Found: C, 63.09; H, 7.81; N, 6.26; S, 7.38; SH, 101%.

EXAMPLES 66–74

Following the procedure of Example 65 but employing the 2-carboxylic acid dipeptide shown in Col. I (which is converted to the corresponding hydroxymethyl compound) and the thiol shown in Col. II one obtains the acylmercapto product shown in Col. III. The R$_6$ ester group can then be removed to yield the desired dipeptide product as the acid. Also, the acyl group can be removed to yield the mercaptan shown in Col. IV.

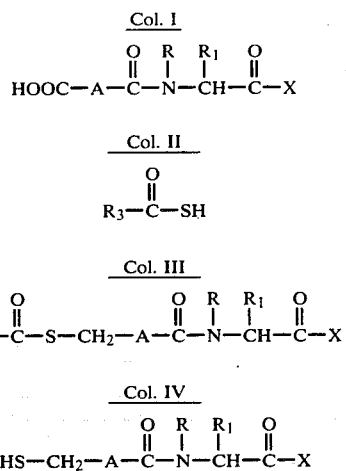

Col. I $$\text{HOOC}-\text{A}-\overset{\overset{\text{O}}{\|}}{\text{C}}-\overset{\overset{\text{R}}{|}}{\text{N}}-\overset{\overset{\text{R}_1}{|}}{\text{CH}}-\overset{\overset{\text{O}}{\|}}{\text{C}}-\text{X}$$

Col. II $$\text{R}_3-\overset{\overset{\text{O}}{\|}}{\text{C}}-\text{SH}$$

Col. III $$\text{R}_3-\overset{\overset{\text{O}}{\|}}{\text{C}}-\text{S}-\text{CH}_2-\text{A}-\overset{\overset{\text{O}}{\|}}{\text{C}}-\overset{\overset{\text{R}}{|}}{\text{N}}-\overset{\overset{\text{R}_1}{|}}{\text{CH}}-\overset{\overset{\text{O}}{\|}}{\text{C}}-\text{X}$$

Col. IV $$\text{HS}-\text{CH}_2-\text{A}-\overset{\overset{\text{O}}{\|}}{\text{C}}-\overset{\overset{\text{R}}{|}}{\text{N}}-\overset{\overset{\text{R}_1}{|}}{\text{CH}}-\overset{\overset{\text{O}}{\|}}{\text{C}}-\text{X}$$

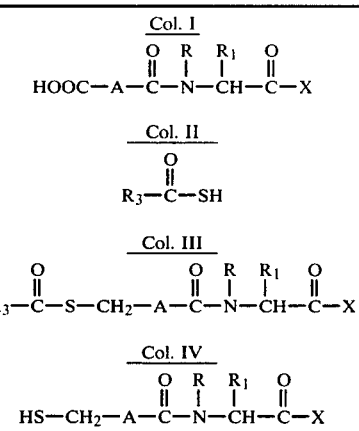

| Example | A | R | $R_1$ | X | $R_3$ |
|---------|---|---|-------|---|-------|
| 72 | naphthyl-C-C- | —H | —CH$_3$ | cyclohexyl-ethyl-N(H)-COOC(CH$_3$)$_3$ (L) | phenyl- |
| 73 | (4-methylphenyl)-C-C- | —H | —CH$_3$ | dithiolane-N(H)-COOC(CH$_3$)$_3$ (L) | phenyl- |
| 74 | naphthyl-C-C- | —H | —CH$_2$-phenyl | —NH—CH(CH$_2$—CH(CH$_3$)$_2$)—COOC(CH$_3$)$_3$ (L) | H$_3$C— |

EXAMPLE 75

(trans)-1-[N-[[(2-Benzoylthio)cyclohexyl]carbonyl]-L-alanyl]-L-proline

To a solution of (trans)-1-[N-[(2-mercaptocyclohexyl)carbonyl]-L-alanyl]-L-proline (328 mg., 1 mmole), from Example 1, in dichloromethane (10 ml.) at 0° under argon is added triethylamine (280 μl, 2.0 mmol.) and benzoyl chloride (120 μl, 1.03 mmole). The mixture is stirred for four hours, warming to room temperature, after which it is diluted with ethyl acetate and washed with 1N hydrochloric acid. The organic phase is dried and concentrated. The residue is chromatographed on silica gel (sili CAR CC-4) using a chloroform to ethyl acetate elution gradient to give (trans)-1-[N-[[(2-benzoylthio)cyclohexyl]carbonyl]-L-alanyl]-L-proline.

EXAMPLES 76–84

Following the procedure of Example 75 but employing the acyl chloride listed below in Col.I one obtains the product shown in Col. II.

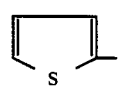

| Example | $R_3$ |
|---------|-------|
| 76 | H$_3$C— |
| 77 | thienyl |

63

-continued

Col. I

R₃—C(=O)—Cl

Col. II

R₃—C(=O)—S—CH₂—CH—C(=O)—NH—CH(L)(CH₃)—C(=O)—N[proline]—COOH (L)

| Example | R₃ |
|---|---|
| 78 | furan-2-yl-CH₂— |
| 79 | 4-pyridyl— |
| 80 | 2-pyridyl-CH₂— |
| 81 | phenyl-CH₂— |
| 82 | 4-Cl-phenyl-(CH₂)₂— |
| 83 | 4-H₃CO-phenyl— |
| 84 | H₅C₂— |

In a similar manner, the procedure of Examples 75 to 84 can be employed with the mercaptan products of Examples 1 to 74 to give other compounds within the scope of the invention.

EXAMPLE 85

(trans)-1-[N-[(Acetylthio)cyclohexylcarbonyl]-L-alanyl]-L-proline is treated with the reagent listed below in Col. I to give the product shown in Col. II.

Col. II

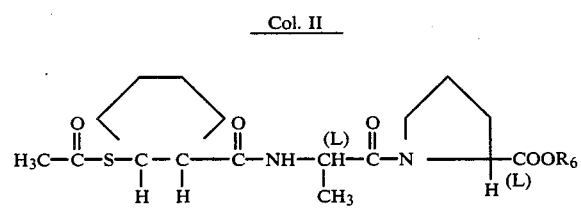

Deacylation with ammonia yields the corresponding mercaptan product.

64

| Example | Col. I | R₆ |
|---|---|---|
| 86 | Cl—CH(cyclohexyl)—O—C(=O)—C₂H₅ | —CH(cyclohexyl)—O—C(=O)—C₂H₅ |
| 87 | Cl—CH(CH(CH₃)₂)—O—C(=O)—C₂H₅ | —CH(CH(CH₃)₂)—O—C(=O)—C₂H₅ |
| 88 | Cl—CH₂—O—C(=O)—C(CH₃)₃ | —CH₂—O—C(=O)—C(CH₃)₃ |
| 89 | Br—CH₂—O—C(=O)—CH₃ | —CH₂—O—C(=O)—CH₃ |
| 90 | Cl—CH₂—O—C(=O)—phenyl | —CH₂—O—C(=O)—phenyl |
| 91 | I—CH₂—C(=O)—O—C(CH₃)₃ | —CH₂—C(=O)—O—C(CH₃)₃ |
| 92 | I—C(CH₃)₂—C(=O)—O—CH₃ | —C(CH₃)₂—C(=O)—O—CH₃ |
| 93 | CH(OH)[CH₂—O—CH(phenyl)₂]₂ | —CH(CH₂—OH)₂ |
| 94 | CH₂(OH)—CH(O—CH(phenyl)₂)—CH₂—O—CH(phenyl)₂ | —CH₂—CH(OH)—CH₂—OH |
| 95 | HO—CH₂—CH₂—N(CH₃)₂ | —CH₂—CH₂—N(CH₃)₂ |
| 96 | HO—(CH₂)₂-(4-pyridyl) | —(CH₂)₂-(4-pyridyl) |
| 97 | HO—(CH₂)₃-(pyridyl) | —(CH₂)₃-(pyridyl) |
| 98 | HO—(CH₂)₂-(3-pyridyl) | —(CH₂)₂-(3-pyridyl) |

In the case of Examples 93 to 98 the reaction with the reagent listed in Col. I is performed in the presence of a coupling agent such as dicyclohexylcarbodiimide and the optional presence of a catalyst such as 4-dimethylaminopyridine.

EXAMPLE 99

(trans)-N,N'-[(2,2'-Dithiobiscyclohexyl)carbonyl]-1,1'-bis[L-alanyl-L-proline]

(trans)-1-[N-[(2-Mercaptohexyl)carbonyl]-L-alanyl]-L-proline is dissolved in water and the pH is adjusted to 6.5 with 1N sodium hydroxide. An ethanolic solution of iodine is added dropwise while maintaining the pH at 6.5 with the careful addition of 1N sodium hydroxide. After the reaction is completed (TLC), the reaction mixture is acidified with concentrated hydrochloric acid and extracted with ethyl acetate. The organic phase is washed with water, dried, and concentrated to dryness to yield (trans)-N,N'-[(2,2'-dithiobiscyclohexyl)carbonyl]-1,1'-bis[L-alanyl-L-proline].

In a similar manner, symmetrical disulfides can be prepared for the compounds of Examples 1 to 98.

EXAMPLE 100

(trans)-1-[N-[(2-Mercaptocyclohexyl)carbonyl]-L-alanyl]-L-proline, monosodium salt (isomer A)

(trans)-1-[N-[(2-Mercaptocyclohexyl)carbonyl]-L-alanyl]-L-proline (isomer A) (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm.×60 cm.) of Sephadex chromatography gel G-10 and eluted with water. Fractions containing the desired product are pooled and lyophilized to give (trans)-1-[N-[(2-mercaptocyclohexyl)carbonyl]-L-alanyl]-L-proline, monosodium salt (isomer A).

EXAMPLE 101

1000 tablets each containing the following ingredients:

| | |
|---|---|
| (trans)-1-[N—[(2-Mercaptocyclohexyl)carbonyl]-L-alanyl]-L-proline, monosodium salt (isomer A) | 100 mg. |
| Corn starch | 50 mg. |
| Gelatin | 7.5 mg. |
| Avicel(microcrystalline cellulose) | 25 mg. |
| Magnesium stearate | 2.5 mg. |
| | 185 mg | are prepared from sufficient bulk quantities by mixing the (trans)-1-[N-[(2-mercaptocyclohexyl)carbonyl]-L-alanyl]-L-proline, sodium salt (isomer A) and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 99 can be prepared.

A similar procedure can be employed to form tablets containing 50 mg. of active ingredient.

EXAMPLE 102

Two piece #1 gelatin capsules each containing 50 mg. of (trans)-N-[N-[(2-mercaptocyclohexyl)carbonyl]-L-phenylalanyl-L-leucine, monosodium salt (isomer A) are filled with a mixture of the following ingredients:

| | |
|---|---|
| (trans)-N—[N—[(2-Mercaptocyclohexyl)carbonyl]-L-phenylalanyl]-L-leucine, monosodium salt (isomer A) | 50 mg. |
| Magnesium stearate | 7 mg. |
| Lactose | 193 mg. |
| | 250 mg. |

In a similar manner capsules containing 50 mg. of the product of any of Examples 1-5, and 7 to 100 can be prepared.

EXAMPLE 103

An injectable solution is prepared as follows:

| | |
|---|---|
| N—[N—(2-Mercaptobenzoyl)-L-phenylalanyl]-L-leucine, monosodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 3 and 5 to 100.

EXAMPLE 104

1000 tablets each containing the following ingredients:

| | |
|---|---|
| (trans)-1-[N—[(2-Mercaptocyclohexyl)carbonyl]-L-alanyl]-L-proline, monosodium salt (isomer A) | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the (trans)-1-[N-[(2-mercaptocyclohexyl)carbonyl]-L-alanyl]-L-proline, monosodium salt (isomer A), Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 99.

What is claimed is:

1. A compound of the formula

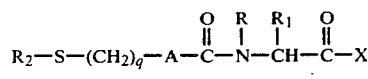

or a pharmaceutically acceptable salt thereof wherein:
A is

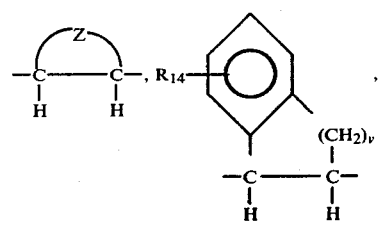

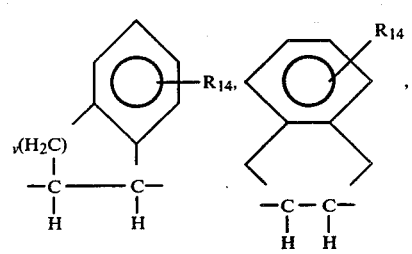

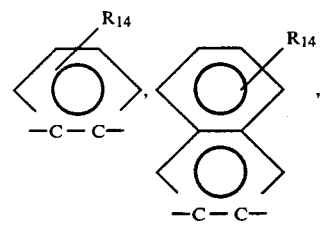

v is one or two;
Z completes a cycloalkyl ring of 3 to 10 carbons; said cycloalkyl ring in which one of the carbon atoms is substituted by a lower alkyl of 1 to 4 carbons, lower alkoxy of 1 to 4 carbons, lower alkylthio of 1 to 4 carbons, phenyl, benzyl, halo, trifluoromethyl, or hydroxy group; or a cycloalkenyl ring of 5 to 7 carbons;
X is an amino or imino acid of the formula

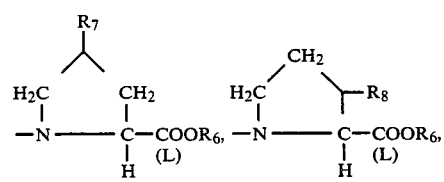

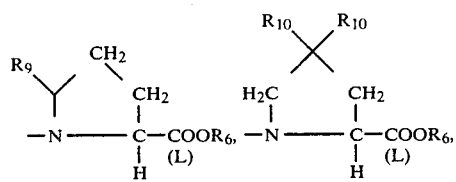

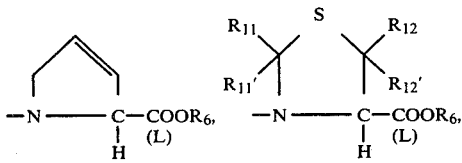

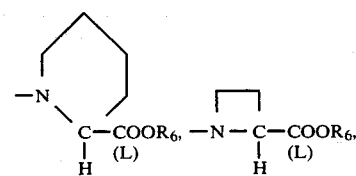

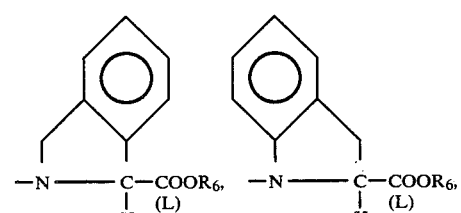

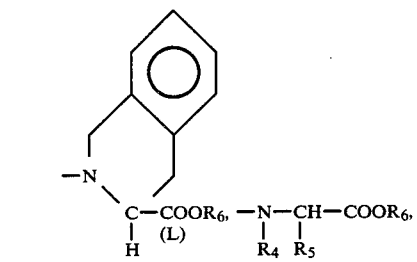

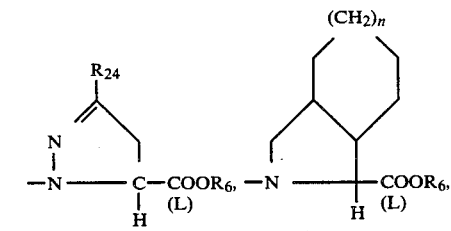

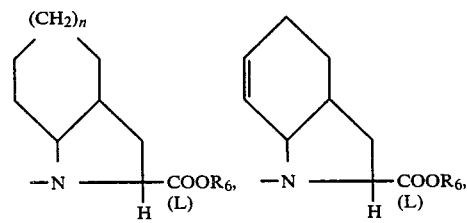

-continued
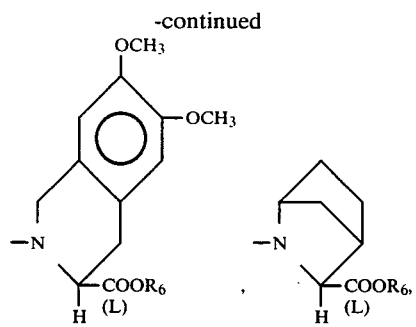
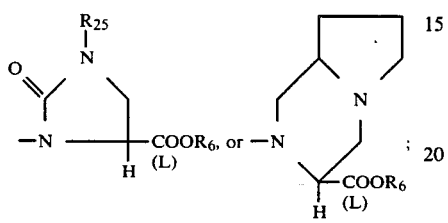
n is zero, one, or two;
$R_{25}$ is lower alkyl of 1 to 4 carbons
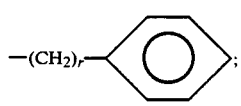
$R_7$ is hydrogen, lower alkyl, halogen,
hydrogen, lower alkyl, halogen, hydroxy,
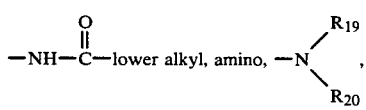
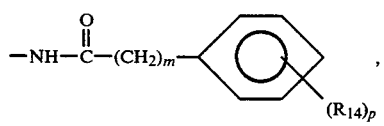
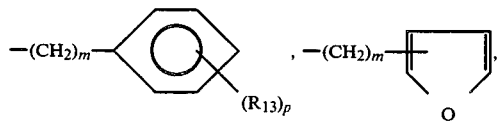
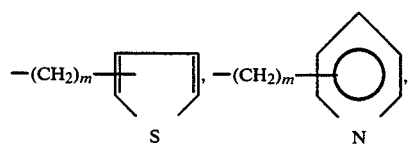
a 1- or 2-naphthyl of the formula
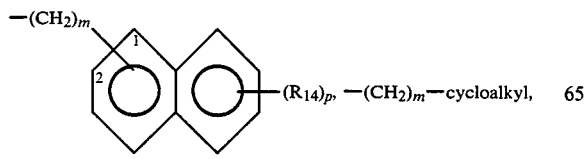
-continued
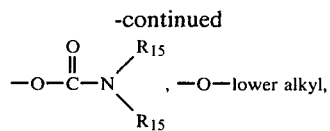, —O—lower alkyl,
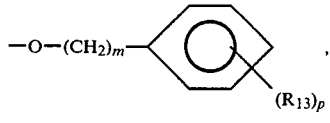
a 1- or 2-naphthyloxy of the formula
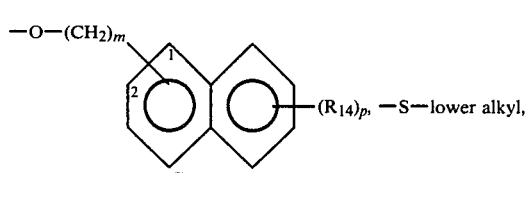, —S—lower alkyl,
of the formula 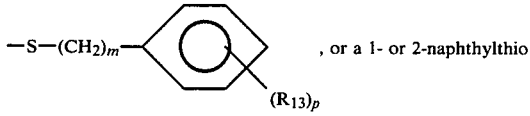
$R_8$ is halogen, 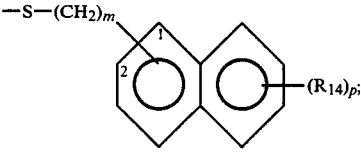
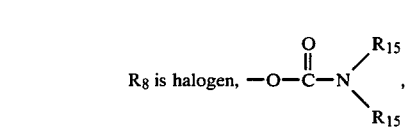, —O—lower alkyl, a 1- or
2-naphthyloxy of the formula
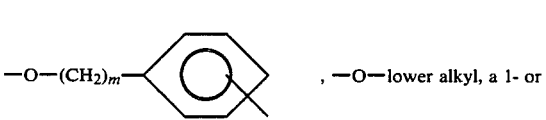
—S—lower alkyl, 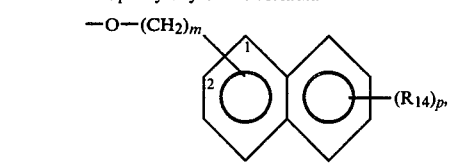,
or a 1- or 2-naphthylthio of the formula
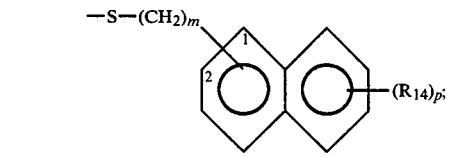

-continued

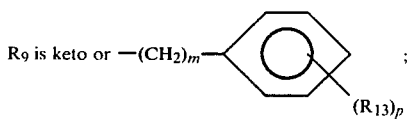

$R_{10}$ is halogen or —Y—$R_{16}$; selected from hydrogen and lower alkyl or $R'_{11}$, $R_{12}$ and $R'_{12}$ are hydrogen and $R_{11}$ is

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two, three, or four;

p is one, two or three provided that p is more than one only if $R_{13}$ or $R_{14}$ is hydrogen, methyl, methoxy, chloro, or fluoro;

$R_{15}$ is hydrogen or lower alkyl of 1 to 4 carbons;

Y is oxygen or sulfur;

$R_{16}$ is lower alkyl of 1 to 4 carbons,

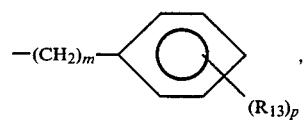

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent;

$R_4$ is hydrogen, lower alkyl,

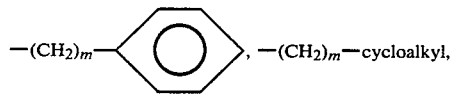

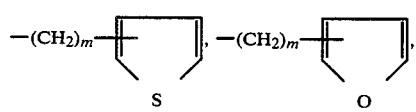

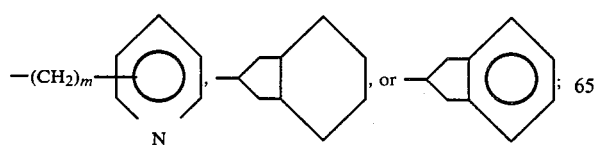

$R_5$ is hydrogen, lower alkyl, 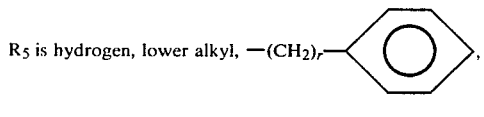

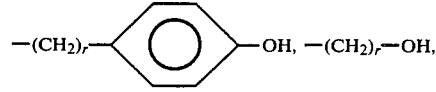

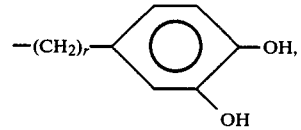

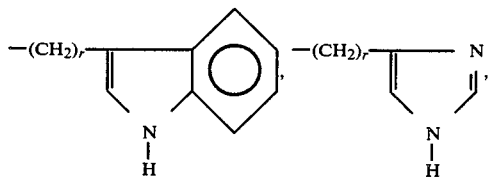

—$(CH_2)_r$—$NH_2$, —$(CH_2)_r$—SH, —$(CH_2)_r$—S—lower alkyl,

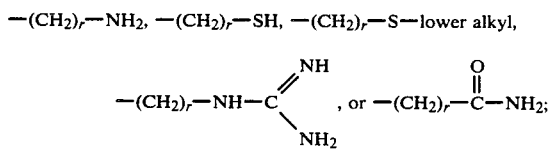

r is an integer from 1 to 4;

$R_{19}$ is lower alkyl, benzyl, or phenethyl;

$R_{20}$ is hydrogen, lower alkyl, benzyl or phenethyl;

R is hydrogen, lower alkyl, cycloalkyl,

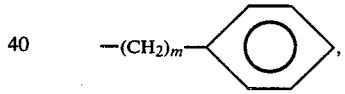

—$(CH_2)_2$—$NH_2$, —$(CH_2)_3$—$NH_2$, —$(CH_2)_4$—$NH_2$,
—$(CH_2)_2$—OH, —$(CH_2)_3$—OH, —$(CH_2)_4$—OH,
—$(CH_2)_2$—SH, —$(CH_2)_3$—SH, or —$(CH_2)_4$—SH;

$R_1$ is hydrogen, lower alkyl, halo substituted lower alkyl,

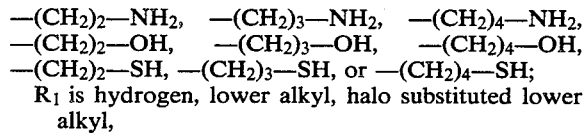

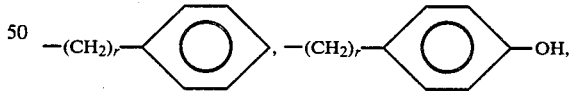

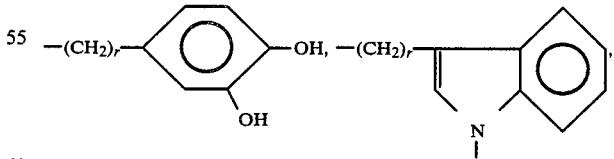

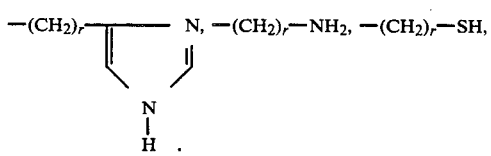

—$(CH_2)_r$—OH, —$(CH_2)_r$—S—lower alkyl,

-continued

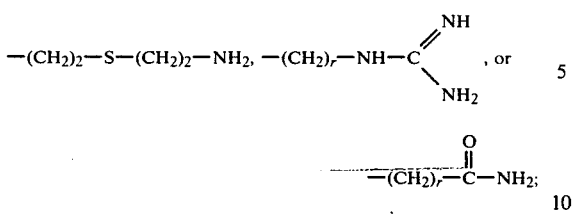

$R_2$ is hydrogen,

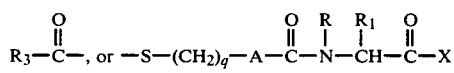

to form a symmetrical disulfide;
$R_3$ is lower alkyl,

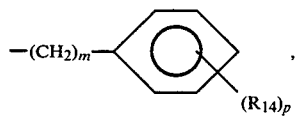

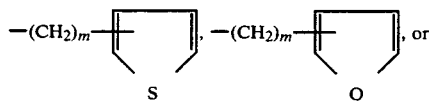

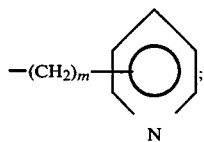

$R_6$ is hydrogen, lower alkyl, benzyl, benzhydryl, a pharmaceutically acceptable salt ion,

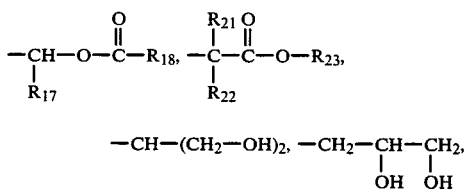

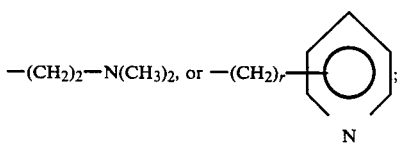

$R_{17}$ is hydrogen, lower alkyl, cycloalkyl, or phenyl;
$R_{18}$ is hydrogen, lower alkyl, lower alkoxy, or phenyl or $R_{17}$ and $R_{18}$ is taken together are —(CH$_2$)$_2$—, —(CH$_2$)$_3$—, —CH=CH—, or

$R_{21}$ and $R_{22}$ are independently selected from hydrogen and lower alkyl;

$R_{23}$ is lower alkyl;
$R_{24}$ is hydrogen, lower alkyl,

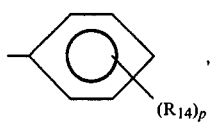

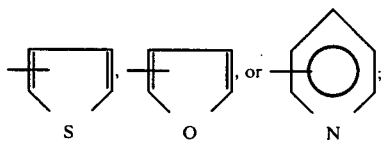

and q is zero or one.
2. A compound of claim 1 wherein:
R is hydrogen or straight or branched chain lower alkyl of 1 to 4 carbons;
$R_1$ is hydrogen, straight or branched chain lower alkyl of 1 to 4 carbons, CF$_3$, —(CH$_2$)$_r$—NH$_2$,

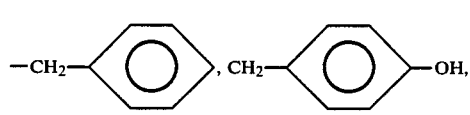

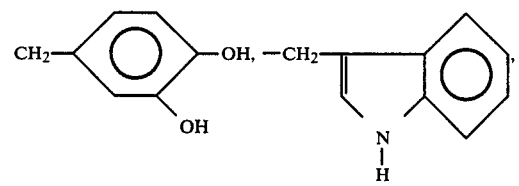

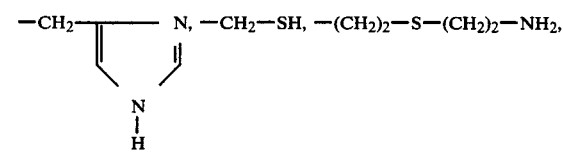

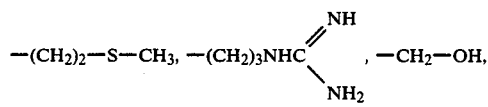

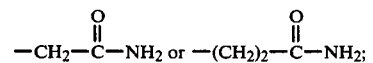

$R_4$ is hydrogen, cyclohexyl, or phenyl;
$R_5$ is hydrogen, straight or branched chain lower alkyl of 1 to 4 carbons,

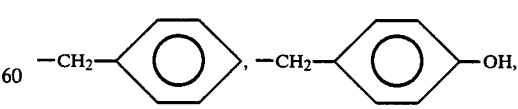

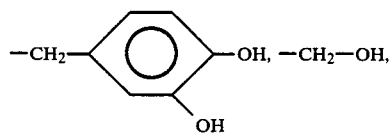

-continued

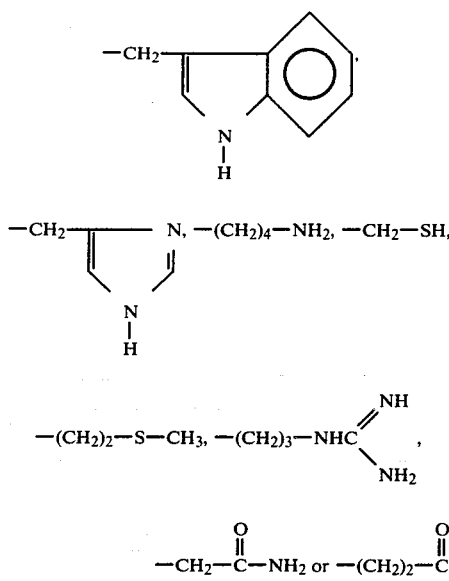

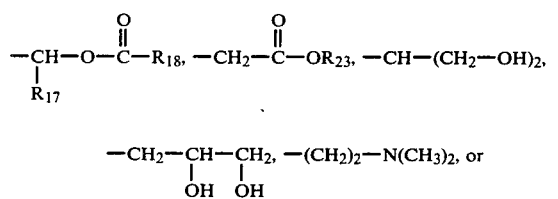

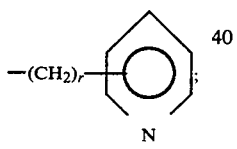

R6 is hydrogen, straight or branched chain lower alkyl of 1 to 4 carbons, an alkali metal salt ion,

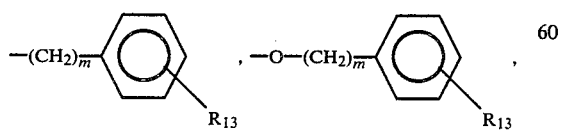

R17 is hydrogen, straight or branched chain lower alkyl of 1 to 4 carbons, or cyclohexyl;
R18 is straight or branched chain lower alkyl of 1 to 4 carbons or phenyl;
R23 is straight or branched chain lower alkyl of 1 to 4 carbons;
R7 is hydrogen, hydroxy, straight or branched chain lower alkyl of 1 to 4 carbons, cyclohexyl, amino, —O—lower alkyl wherein lower alkyl is straight or branched chain of 1 to 4 carbons,

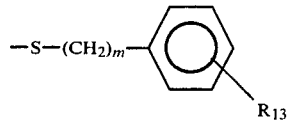

1-naphthyloxy, 2-naphthyloxy, —S—lower alkyl wherein lower alkyl is straight or branched chain of 1 to 4 carbons,

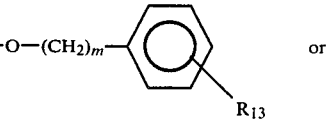

1-naphthylthio, or 2-naphthylthio;
R8 is —O—lower alkyl, —S—lower alkyl,

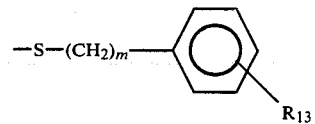

wherein lower alkyl is straight or branched chain of 1 to 4 carbons,
R9 is phenyl, 2-hydroxyphenyl or 4-hydroxyphenyl;
R10 are both fluoro, both chloro or both —Y—R16;
Y is O or S;
R16 is straight or branched chain lower alkyl of 1 to 4 carbons or the R16 groups join to complete an unsubstituted 5- or 6-membered ring or said ring in which one or more of the available carbons has a methyl or dimethyl substituent;
R11, R11', R12 and R12' are all hydrogen or R11 is phenyl, 2-hydroxyphenyl, or 4-hydroxyphenyl and R11', R12 and R12' are all hydrogen;
r is an integer from 1 to 4;
m is zero, one, or two;
R13 is hydrogen, methyl, methoxy, methylthio, chloro, bromo, fluoro, or hydroxy;
R14 is hydrogen, methyl, methoxy, methylthio, chloro, bromo, fluoro, or hydroxy; and
R24 is phenyl.

3. A compound of claim 2 wherein:

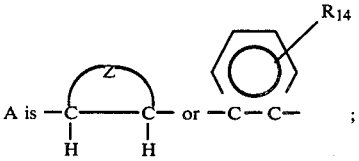

Z completes a cycloalkyl ring of 4 to 7 carbons or a cycloalkyl ring of 4 to 7 carbons wherein one of the carbons is substituted by a methyl, methoxy, methylthio, phenyl, benzyl, Cl, Br, F, or hydroxy;
R14 is hydrogen, methyl, methoxy, methylthio, Cl, Br, F, or hydroxy; and
R2 is hydrogen,

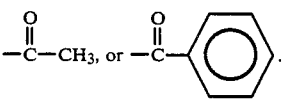

4. A compound of claim 3 wherein:
X is $$-\text{N}-\text{CH}-\text{COOR}_6, \quad \begin{array}{c} \text{R}_7 \\ \text{H}_2\text{C}-\text{CH} \\ | \quad \quad | \\ \text{R}_4 \text{ R}_5 \end{array} \begin{array}{c} \text{CH}_2 \\ | \\ -\text{N}-\text{C}-\text{COOR}_6 \\ | \\ \text{H} \quad \text{(L)} \end{array} ,$$

[structure with (CH₂)ₜ bridge and two S atoms, H₂C-CH₂ group, —N—C—COOR₆ (L)], or [tetrahydroisoquinoline-like structure with —N—, CH₂, COOR₆ (L)];

R is hydrogen or methyl;
R₁ is hydrogen, methyl, benzyl, or —(CH₂)₄—NH₂;
R₆ is hydrogen, straight or branched chain lower alkyl or 1 to 4 carbons, or an alkali metal salt ion;
R₄ is cyclohexyl or phenyl and R₅ is hydrogen or R₄ is hydrogen and R₅ is methyl, —CH₂—(phenyl), —CH₂—(phenyl)—OH, —CH₂—(phenyl with OH, OH), —CH₂—(indolyl), or —CH₂—(imidazolyl);

R₇ is hydrogen, cyclohexyl, lower alkoxy of 1 to 4 carbons,

—(CH₂)ₘ—(phenyl-R₁₃), —O—(CH₂)ₘ—(phenyl-R₁₃), or —S—(CH₂)ₘ—(phenyl-R₁₃);

m is zero, one or two;
R₁₃ is hydrogen, methyl, methoxy, methylthio, chloro, bromo, fluoro, or hydroxy; and
t is 2 or 3.

5. A compound of claim 4 wherein:
q is zero;
A is

—C—C— (cyclohexyl);
   |  |
   H  H and R₂ is hydrogen.

6. A compound of claim 5 wherein
X is $$-\text{N} \begin{array}{c} \text{R}_7 \\ | \\ -\text{CH} \\ | \\ \text{CH}_2 \end{array} \text{COOR}_6.$$

7. A compound of claim 6 wherein
R₇ is hydrogen;
R₆ is hydrogen or an alkali metal salt ion;
R is hydrogen; and
R₁ is methyl.

8. The compound of claim 7, (trans)-1-[N-[(2-mercaptocyclohexyl)carbonyl]-L-alanyl]-L-proline, monolithium salt.

9. The compound of claim 7, (trans)-1-[N-[(2-mercaptocyclohexyl)carbonyl]-L-alanyl]-L-proline, monolithium salt (isomer A).

10. The compound of claim 7, (trans)-1-[N-[(2-mercaptocyclohexyl)carbonyl]-L-alanyl]-L-proline, monolithium salt (isomer B).

11. A compound of claim 5 wherein
X is $$-\text{NH}-\text{CH}-\text{COOR}_6.$$
$$\quad\quad\quad | $$
$$\quad\quad\quad \text{R}_5$$

12. A compound of claim 11 wherein
R₅ is —CH₂—CH(CH₃)₂;
R₆ is hydrogen or an alkali metal salt ion;
R is hydrogen; and
R₁ is —CH₂—(phenyl).

13. The compound of claim 12, N-[N-[(2-mercaptocyclohexyl)carbonyl]-L-phenylalanyl]-L-leucine.

14. The compound of claim 12, (trans)-N-[N-(2-mercaptocyclohexyl)carbonyl]-L-phenylalanyl]-L-leucine (isomer A).

15. The compound of claim 12, (trans)-N-[N-(2-mercaptocyclohexyl)carbonyl]-L-phenylalanyl]-L-leucine (isomer B).

16. A compound of claim 4 wherein:
q is zero;
A is

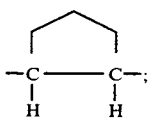

and R₂ is hydrogen.

17. A compound of claim 16 wherein:

X is

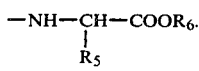

18. A compound of claim 17 wherein:

R₅ is —CH₂—CH(CH₃)₂;

R₆ is hydrogen or an alkali metal salt ion;

R is hydrogen; and

R₁ is

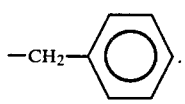

19. A compound of claim 4 wherein:

q is zero;

A is

and R₂ is hydrogen.

20. A compound of claim 19 wherein:

X is

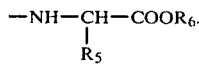

21. A compound of claim 20 wherein:

R₅ is —CH₂—CH(CH₃)₂;

R₆ is hydrogen or an alkali metal salt ion;

R is hydrogen; and

R₁ is

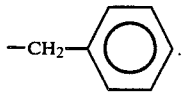

22. A compound of claim 4 wherein:

q is one;

A is

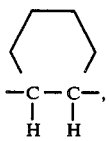

and R₂ is hydrogen.

23. A compound of claim 22 wherein:

X is

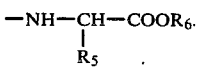

24. A compound of claim 23 wherein:

R₅ is —CH₂—CH(CH₃)₂;

R₆ is hydrogen or an alkali metal salt ion;

R is hydrogen; and

R₁ is

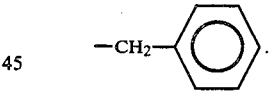

* * * * *